United States Patent
Ishibashi

(10) Patent No.: US 10,925,298 B2
(45) Date of Patent: Feb. 23, 2021

(54) FORMULA FEED

(71) Applicants: K.K. SHIMONITA BUSSAN, Kanagawa (JP); K.K. YUTAKA TRENDS, Tokyo (JP)

(72) Inventor: Shinichiro Ishibashi, Kanagawa (JP)

(73) Assignees: K.K. Shimonita Bussan, Kanagawa (JP); K.K. Yutaka Trends, Tokyo (JP)

( * ) Notice: Subject to any disclaimer, the term of this patent is extended or adjusted under 35 U.S.C. 154(b) by 250 days.

(21) Appl. No.: 16/192,009

(22) Filed: Nov. 15, 2018

(65) Prior Publication Data

US 2019/0150479 A1    May 23, 2019

(51) Int. Cl.
| | | |
|---|---|---|
| *A23K 10/30* | (2016.01) | |
| *A61K 36/888* | (2006.01) | |
| *A23K 50/30* | (2016.01) | |
| *A23K 50/75* | (2016.01) | |
| *A23K 20/20* | (2016.01) | |
| *A23K 20/105* | (2016.01) | |
| *A23K 20/158* | (2016.01) | |

(52) U.S. Cl.
CPC ............ *A23K 10/30* (2016.05); *A23K 20/105* (2016.05); *A23K 20/158* (2016.05); *A23K 20/20* (2016.05); *A23K 50/30* (2016.05); *A23K 50/75* (2016.05); *A61K 36/888* (2013.01); *A61K 2236/15* (2013.01); *Y02P 60/87* (2015.11)

(58) Field of Classification Search
CPC .... A23K 10/30; A23K 20/105; A23K 20/158; A23K 20/20; A23K 50/30; A23K 50/75; A61K 2236/15; A61K 36/888; Y02P 60/87
See application file for complete search history.

(56) References Cited

FOREIGN PATENT DOCUMENTS

| | | | |
|---|---|---|---|
| CN | 201410131162 A | | 6/2014 |
| JP | H07000118 A | | 1/1995 |
| JP | 2004049016 A | | 2/2004 |
| JP | 2008237192 A | * | 10/2008 |
| JP | 2008237192 A | | 10/2008 |

* cited by examiner

*Primary Examiner* — Aaron J Kosar
(74) *Attorney, Agent, or Firm* — DeLio Peterson & Curcio; Thomas E. Ciesco

(57) ABSTRACT

A formula feed for raising pigs with which appetite and body weight can be stimulated in piglets after weaning while decreasing the price, as well as a formula feed for animals, a formula feed for livestock, a formula feed for poultry, a formula feed for pets, and a formula feed for culturing fish. A formula feed characterized in that among a refined powder and a fly powder which are obtained by pulverizing konnyaku (*arum* root), which is a bulb of a plant, the fly powder is added to the formula feed. The fly powder corresponds to 40 to 50% of the total mass of the fly powder and the refined powder. Further, the formula feed is preferably a formula feed for raising pigs to which at least 1% by mass of the fly powder is added. In addition, 1 to 5% by mass of the fly powder may be added.

18 Claims, 6 Drawing Sheets

Chart 7 Control plot

Chart 8 Test area

FORMULA FEED

BACKGROUND OF THE INVENTION

Field of the Invention

The present invention relates to a formula feed that contributes to promotion of growth in animals, a formula feed for raising pigs that contributes to promotion of growth in pigs, a formula feed for raising chickens that contributes to promotion of growth in chickens, a formula feed for other animals, a formula feed for livestock, a formula feed for poultry, a formula feed for pets, and a formula feed for culturing fish.

Description of Related Art

For example, a formula feed is generally used to rear pigs, and after a pig has grown to a body weight necessary for shipment, the pig is supplied to the market. Formula feeds which are necessary for such growth have been increasing in price in recent years, and it has been said that the feed-to-sales ratio (the ratio of feed costs relative to sales) in pig raising management is now 50% or more. Therefore, there is currently a desire to shorten the fattening period. In order to shorten the fattening period, it is considered to be important to stimulate the appetite of piglets after weaning.

Thus, there have been inventions related to formula feed for baby pigs/piglets that promotes the growth of piglets by mixing herbs into a formula feed (for example, Patent Literature 1).

However, if herbs are mixed into a formula feed, the price of such a formula feed will increase further, and this presents a problem in that the feed-to-sales ratio cannot be decreased.

Therein, as a result of earnest research, the present inventors discovered that mixing konnyaku (*arum* root) fly powder, which is normally discarded, into a formula feed enables the price of the formula feed to be decreased and achieves appetite stimulation and body weight promotion in piglets after weaning, and thus the present inventors developed the present invention which can also be applied to other animals.

PRIOR ART LITERATURE

Patent Literature

Patent Literature 1: Japanese Patent No. 4874015

SUMMARY OF INVENTION

Problem to be Solved by Invention

The present invention was created in consideration of the above circumstances, and a problem of the present invention is to provide a formula feed which uses fly powder to decrease the price and promote growth, a formula feed for raising pigs which uses fly powder to decrease the price and stimulate the appetite and promote the body weight of piglets after weaning, a formula feed for raising chickens which promotes growth in baby chicks, a formula feed for other animals, a formula feed for livestock, a formula feed for poultry, a formula feed for pets, and a formula feed for culturing fish.

Means for Solving the Problem

In order to solve the above-described problem, an invention of a formula feed according to claim 1 is characterized in that among a refined powder and a fly powder which are obtained by pulverizing konnyaku, which is a bulb of a plant, the fly powder is added to the formula feed.

An invention of a formula feed according to claim 2 is characterized in that in the invention according to claim 1, the fly powder corresponds to 40 to 50% of the total mass of the fly powder and the refined powder.

An invention of a formula feed according to claim 3 is characterized in that in the invention according to claim 1 or 2, at least 1% by mass of the fly powder is added.

An invention of a formula feed according to claim 4 is characterized in that in the invention according to claim 1 or 2, 1 to 5% by mass of the fly powder is added.

An invention of a formula feed for raising pigs according to claim 5 is characterized in that the formula feed according to any one of claims 1 to 4 is used.

An invention of a formula feed for raising chickens according to claim 6 is characterized in the formula feed according to any one of claims 1 to 4 is used.

Further, the invention may be a formula feed for animals characterized in that the fly powder as recited in any one of claims 1 to 4 is added.

In addition, the invention may be a formula feed for livestock characterized in that the fly powder as recited in any one of claims 1 to 4 is added.

The livestock is preferably a cow, a horse, a donkey, a sheep, a goat, or a boar, etc.

Further, the invention may be a formula feed for poultry characterized in that the fly powder as recited in any one of claims 1 to 4 is added.

The poultry is preferably a chicken, a quail, a duck, a goose, a turkey, a wild duck, a pheasant, a peacock, an ostrich, or an emu, etc.

Further, the invention may be a formula feed for pets characterized in that the fly powder as recited in any one of claims 1 to 4 is added.

The pet is preferably a dog, a cat, a rabbit, a hamster, or a guinea pig, etc.

Further, the invention may be a formula feed for culturing fish characterized in that the fly powder as recited in any one of claims 1 to 4 is added.

The fish is preferably a tuna, a flatfish, a sea bream, a yellowtail, an eel, or a carp, etc.

Effects of Invention

According to the invention recited in Claim 1, konnyaku fly powder, which is normally discarded, is added, and thus the price of the formula feed can be reduced. Further, for example, in an actual test using piglets, results were achieved in which the piglets of the test section which were given a formula feed containing the fly powder exhibited increased average body weight and average daily body weight gain compared to the piglets of the control section which were given a formula feed that does not contain the fly powder as shown in Tables 5, 8, and 9 and FIGS. 2 to 4. In addition, for example, in a test using baby chicks, growth was clearly promoted as shown in FIGS. 7 and 8. Therefore, animal growth can be promoted while decreasing the price of the formula feed. Moreover, the meat taste was also clearly enhanced in a test using chickens.

According to the invention recited in Claim 2, the fly powder corresponds to 40 to 50% of the total mass of the fly powder and the refined powder. Thus, a large amount of fly powder is generated during the course of producing the refined powder, and this fly powder can be effectively utilized.

According to the invention recited in Claim 3, it is sufficient to add at least 1% by mass of the fly powder. Therefore, there is no need to secure a large space for storing the fly powder, and even if the fly powder is purchased for a fee, the purchase cost can be kept low. Further, by adding 1% by mass of the fly powder, for example, the appetite, average body weight, and average daily body weight gain of the piglets can be increased as shown in the test results given in Tables 5, 8, and 9 and FIGS. 2 to 4. Moreover, the growth of baby chicks can be promoted as shown in FIGS. 7 and 8.

According to the invention recited in Claim 4, 1 to 5% by mass of the fly powder is added. Therefore, if a large amount of surplus fly powder exists, setting the amount of fly powder to be added to 5% by mass achieves an effect in which a larger amount of the fly powder can be effectively utilized and the amount of normal formula feed to be used can be kept low.

According to the invention of a formula feed for raising pigs recited in Claim 5, konnyaku fly powder, which is normally discarded, is added, and thus the price of the formula feed for raising pigs can be reduced. Further, for example, in an actual test, results were achieved in which the piglets of the test section which were given a formula feed for raising pigs containing the fly powder exhibited increased average body weight and average daily body weight gain compared to the piglets of the control section which were given a formula feed for raising pigs that does not contain the fly powder as shown in Tables 5, 8, and 9 and FIGS. 2 to 4.

The above test was conducted over 8 weeks after an acclimation period of 1 week had passed after weaning. During the first 4 weeks from the start of the test, as shown in, for example, FIG. 2, the results showed that the body weight of the piglets in the test section had increased with a considerable body weight difference compared to the body weight of the piglets in the control section. Further, during the following four weeks from the end of the 4$^{th}$ week until the end of the 8$^{th}$ week, although the increasing trend in the body weight difference slowed down slightly, the body weight of the piglets in the test section still showed a tendency to increase with a considerable body weight difference compared to the body weight of the piglets in the control section. Moreover, from FIG. 2, it can be understood that the tendency of the body weight of the piglets in the test section to increase with a considerable body weight difference compared to the body weight of the piglets in the control section continued after the end of the 8$^{th}$ week.

Upon observing 5 of the piglets in the test section and 5 of the piglets in the control section which had an initial body weight of less than 8.5 Kg at the start of the test, the average daily body weight gain during the first 4 weeks was 0.617 Kg/piglet/day in the test section and 0.507 Kg/piglet/day in the control section as shown in FIG. 4, and the difference therebetween was 0.110 Kg/piglet/day. On the other hand, when examining the average daily body weight gain during the first 4 weeks for all of the pigs in the test including the 8 pigs in the test section and the 8 pigs in the control section, a difference of 0.069 Kg/piglet/day between the test section and the control section was observed as shown in FIG. 3. Therefore, it can be understood that the effect of body weight increase achieved by the konnyaku fly powder is higher in piglets of lower body weight. In other words, the effect of increasing the body weight achieved by mixing the fly powder into the formula feed is higher in more immature piglets.

As a cause leading to the above results, it is believed that cellulose and glucomannan included in the fly powder increase good bacteria such as *Bifidobacterium* which improve the intraintestinal environment, and conversely reduce bad bacteria such as aerobic bacteria which worsen the intraintestinal environment. In fact, in a test regarding the feces of the piglets, it was observed as shown in FIG. 5 that *Bacteroides* and *Bifidobacterium*, which are good bacteria, were increased in the test section compared to the control section, and it was observed that aerobic bacteria and anaerobic bacteria, which are bad bacteria, were decreased in the test section compared to the control section.

It is also believed that lactic acid and acetic acid are increased by *Bifidobacterium*, and this promotes intraintestinal acidification and suppresses the proliferation of bad bacteria. In fact, in the test regarding the feces of the piglets, as shown in FIG. 6($a$), the pH of the control section was nearly neutral at 6.90, whereas the pH of the test section was slightly acidic at 6.30.

In addition, in a test regarding moisture contained in the feces, as shown in FIG. 6($b$), the feces of the piglets in the test section clearly contained a larger amount of moisture than the control section. Therefore, since the feces of the piglets in the test section contained more moisture, it is believed that the bowel movements in these piglets had improved, and thus the body weight of these piglets improved together with an improvement in their physical condition.

In the period during which piglets transition from weaning feed to regular formula feed such as the period of 4 weeks from the start of the test, it is extremely important to acclimate the stomach and bowels, etc. to the regular formula feed and to adjust the formula feed in order to decrease stress and improve the physical condition, which promotes the future growth of the piglets. The formula feed for raising pigs to which fly powder has been added can promote the growth of piglets during this important period, and this enables the period until shipment to be shortened, the formula feed consumption amount to be reduced, and the feed-to-sales ratio to be decreased, etc.

The raw material of the konnyaku fly powder is konnyaku, which is a bulb of a plant, and thus the konnyaku fly powder can serve as an extremely safe raw material for a formula feed for raising pigs.

According to the invention of a formula feed for raising chickens recited in claim 6, growth was clearly promoted in the baby chicks of the test section which received the fly powder (FIG. 8) compared to the baby chicks which did not receive the fly powder (FIG. 7). In other words, growth of the baby chicks can be promoted while decreasing the price of the formula feed. Moreover, the taste of the meat was also clearly improved by the formula feed for raising chickens.

Operational effects similar to those of the inventions according to claims 1 to 4 are also achieved when the invention is a formula feed for animals, a formula feed for livestock, a formula feed for poultry, a formula feed for pets, or a formula feed for culturing fish instead of the formula feed for raising pigs.

BRIEF DESCRIPTION OF DRAWINGS

FIG. 6A is a graph illustrating test results of fecal characteristics regarding pH, FIG. 6B is a graph illustrating test results of fecal characteristics regarding moisture, FIG. 6C is a graph illustrating test results of decomposed matter regarding the content of ammonia, FIG. 6D is a graph illustrating test results of decomposed matter regarding the content of p-cresol, FIG. 6E is a graph illustrating test results of decomposed matter regarding the content of 4-ethylphenol, FIG. 6F is a graph illustrating test results of decomposed matter regarding the content of indole, and FIG. 6G is a graph illustrating test results of decomposed matter regarding the content of skatole.

DESCRIPTION OF EMBODIMENTS

Figure 1:
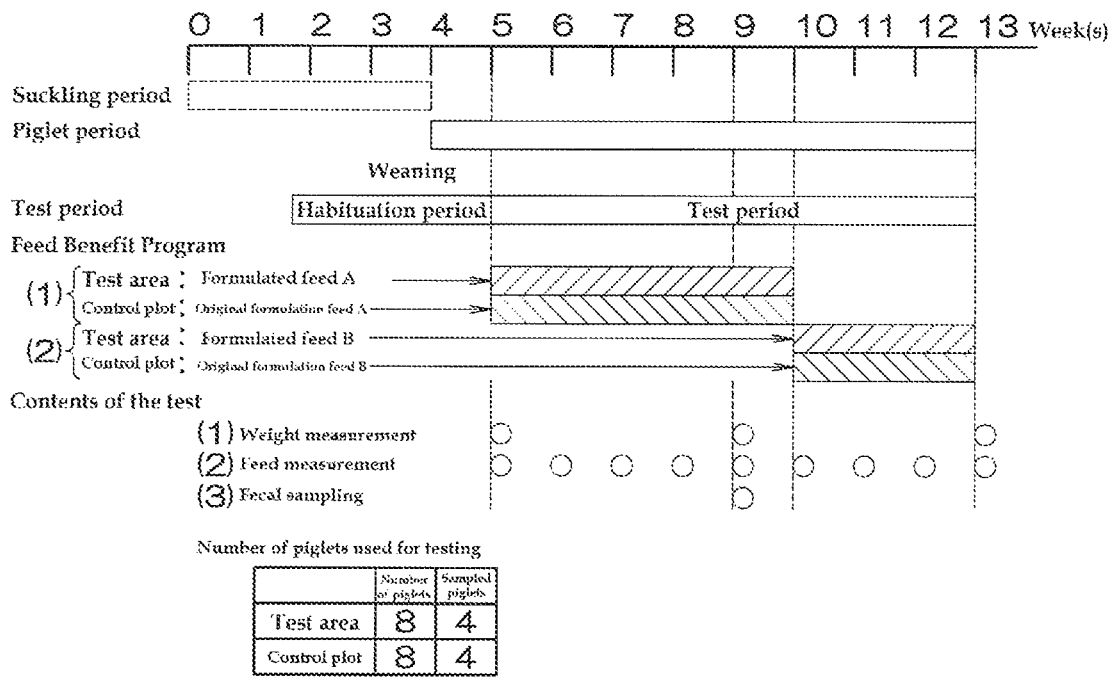
FIG. 1 is an explanatory diagram illustrating a test plan using a formula feed configured as a formula feed for raising pigs which contains fly powder according to a first embodiment of the present invention, and a stock formula feed which does not contain fly powder.

A formula feed for raising pigs according to a first embodiment of the present invention will now be explained in detail below referring to the drawings.

The formula feed for raising pigs according to the present embodiment is characterized in that among a refined powder and a fly powder, which are konnyaku powders formed upon mechanically pulverizing konnyaku which is a bulb of a plant, the formula feed contains the fly powder. Further, the formula feed for raising pigs is characterized in that the fly powder corresponds to 40 to 50% of the total mass of the fly powder and the refined powder. In addition, the formula feed for raising pigs is characterized in that the fly powder is added in an amount of 1% by mass of the stock formula feed.

Edible konnyaku is normally made using, as a raw ingredient, the refined powder among konnyaku powders obtained upon pulverizing the above-mentioned konnyaku which is a bulb. The ratio of refined powder to fly powder is from 6:4 to 5:5 (document source: refer to the master's thesis from 2002 of Kaori Ishikawa, Graduate School of Kochi University of Technology). In other words, the ratio of the fly powder corresponds to 40 to 50% by mass of the konnyaku powders (the total mass of the refined powder and the fly powder).

The components of the fly powder include 4% by mass of water, 17% by mass of proteins, and 60 to 65% by mass of sugars (refer to Table 5 of the above-mentioned master's thesis). In this case, if the sugar content is 65% by mass, the breakdown thereof is 23% by mass of a water-soluble portion and 42% by mass of a non-water-soluble portion (refer to Table 5 of the above-mentioned master's thesis). In other words, the water-soluble portion of the total fly powder is 40% by mass, and the non-water-soluble portion of the total fly powder is 60% by mass. Therefore, among the 40% by mass water-soluble portion, 23% by mass thereof is sugars, and among the 60% by mass non-water-soluble portion, 42% by mass thereof is sugars.

The breakdown of the 23% by mass of sugars in the water-soluble portion is as follows: 12 to 15 (average 13.5) % by mass (18.4% by mass in HPLC ratio) of glucomannan in dry mass; and 8 to 11 (average 9.5) % by mass (4.6% by mass in HPLC ratio) of unknown sugars in dry mass (refer to FIG. 5 of the above-mentioned master's thesis). Meanwhile, the breakdown of the 42% by mass of sugars in the non-water-soluble portion is as follows: 31.2% by mass of starch; 7.2% by mass of cellulose; and 3.6% by mass of unknown sugars (refer to FIG. 5 of the above-mentioned master's thesis).

The portion other than the 23% by mass of sugars among the 40% by mass water-soluble portion is 17% by mass of lipids, proteins, inorganic components, etc. (refer to FIG. 5 of the above-mentioned master's thesis). Meanwhile, the portion other than the 42% by mass of sugars among the 60% by mass non-water-soluble portion is 18% by mass of lipids, proteins, inorganic components, etc. (refer to FIG. 5 of the above-mentioned master's thesis).

Therefore, 13.5 (average value) % by mass of glucomannan in dry mass and 7.2% by mass of cellulose are included in the total fly powder.

As the above-mentioned stock formula feed containing fly powder, a formula feed containing components suited for piglets after weaning is used. Specifically, "Mama 8 Grandy W" (product name) from Feedone Co., Ltd. is used as a Stock Formula Feed A, and "Kodawari Pork" (product name) from Feedone Co., Ltd. is used as a Stock Formula Feed B. The components of Stock Formula Feed A, i.e. "Mama 8 Grandy W", consist of the portion remaining upon removing the konnyaku fly powder from a Formula Feed A as shown in Table 1, and the components of Stock Formula Feed B, i.e. "Kodawari Pork", consist of the portion remaining upon removing the konnyaku fly powder from a Formula Feed B as shown in Table 1. However, in Table 1, the raw ingredients in parentheses indicate that there are cases in which those raw ingredients are not used due to circumstances of the raw ingredients, etc.

In this example, Formula Feed A corresponds to a formula feed for raising pigs according to the present invention obtained by adding konnyaku fly powder in an amount of 1% of the total mass to Stock Formula Feed A "Mama 8 Grandy W". Further, Formula Feed B corresponds to a formula feed for raising pigs according to the present invention obtained by adding konnyaku fly powder in an amount of 1% of the total mass to Stock Formula Feed B "Kodawari Pork".

TABLE 1

Components of Compound Feeds

| Classification of Raw Materials | Raw Materials | Compounding ratio (Mass %) | | | |
|---|---|---|---|---|---|
| | | Compound feed A Test area | Original formula feed A Control plot | Compound feed B Test area | Original formula feed B Control plot |
| Grain | Field Corn, Heat-treated Corn, Wheat, Flour, (Toasted Soybean Flour), (Extruder-treated Soybeans) | 54 | ← | | |
| Botanical Oil Residue | Soybean Oil Residue, Dehulled-Soybean Oil Residue, (Extruder-treated Soybean Oil Residue), (Corn Jam Meal) | 19 | ← | | |
| Zooidal Compound Feed | Skimmilk Powder, Fish Meal, Dried Whey, (Concentrated Whey Protein) | 12 | ← | | |
| Other | Confectionary, Animal Oil and Fat, Common Salt, Calcium Phosphate, Calcium Carbonate, Lactic Acid, Diatomaceous Earth, Citric Acid, *Aspergillus* Fermenting Substance, Galactoorigosaccharide Sirup, BakeryYeast, Silicic Acid, Anise Seed Oil, Anise Seed, Milk Thistle, Garlic, Lactose, Glucose, Vegetable Fat and Oil | 15 | ← | | |
| Grain | Corn, Wheat flour, Soy bean, Sweet potato, (Cassava), (Rye) | | | 80 | ← |
| Botanical Oil Residue | Soy bean meal | | | 15 | ← |
| Chaff and Bran | Rice bran | | | 1 | ← |
| Other | Coconut fruit endosperm lees, Calcium carbonate Calcium phosphate, Salt, Citric acid, Silicic acid, Diatomaceous earth, Lactic acid, (Animal oils for industrial purposes), (Coir), (Vegetable oils) | | | 4 | ← |
| | *Konjac* flour scattering | 1 | — | 1 | — |
| | Total | 101 | 100 | 101 | 100 |

In the results of preliminary testing conducted with piglets using Formula Feeds A' and B', which were obtained by adding 5% by mass of konnyaku fly powder to Stock Formula Feeds A and B, there were no problems with the palatability of Formula Feeds A' and B', and the piglets in the test section which were given Formula Feeds A' and B' were superior in terms of development body weight, amount of feed ingested, and feed demand rate compared to the piglets in the control section which were given Stock Formula Feeds A and B. Therein, considering these results, tests regarding the growth results, number of fecal bacteria, and fecal characteristics of piglets were conducted using Formula Feeds A and B to which 1% by mass of the konnyaku fly powder was added, and the content and results of these tests shall be explained below.

(1) Test Facility
Name: Pioneer Farm of Toyoura Veterinary Clinic, Co., Ltd.
Location: 1816 Kamifurusawa, Atsugi-shi, Kanagawa-ken
Representative Director: Munetaka Oi
(2) Test Personnel
Test Responsible Party: Takashi Nakamura, Chief Veterinarian
Person in Charge of Execution: Akiko Daiku
(3) Test Execution Period
Jun. 14, 2016 to Aug. 9, 2016

(4) Formula Feed for Raising Pigs
(i) Stock Formula Feeds A and B
Stock Formula Feeds A and B were prepared by Toyoura Veterinary Clinic, Co., Ltd.
(ii) Konnyaku Fly Powder
The konnyaku fly powder was prepared by "Shinichiro Ishihashi", an inventor of the present invention.
(iii) Formula Feeds A and B
Formula Feed A was prepared at Toyoura Veterinary Clinic, Co., Ltd. by adding and uniformly mixing the konnyaku fly powder (1% by mass) into Stock Formula Feed A (100% by mass), and Formula Feed B was prepared at Toyoura Veterinary Clinic, Co., Ltd. by adding and uniformly mixing the konnyaku fly powder (1% by mass) into Stock Formula Feed B (100% by mass).
(5) Specimen Pigs
Two litters (16 piglets) of weaned piglets (body weight of 7 Kg, around 27 days after birth) were submitted for testing. All of the piglets were tagged beforehand so that each individual could be surely identified. As shown in FIG. 1, the nursing period was 4 weeks, and after 4 weeks had elapsed (i.e. after weaning), a 1 week acclimation period was established in which the 16 piglets were raised together with normal feed (Mama 8 Grandy W). The test was initiated after this acclimation period. The testing sections were assigned considering each litter and the body weight and weight gain during the acclimation period so that the test section and the control section would be even (so that no bias would occur). The test section and the control section were each assigned 8 piglets. However, the piglets were not divided by male (c) and female (9). For the fecal test, 4 piglets were selected from each section considering each litter so as to achieve evenness between the two sections (so that no bias would occur). With regard to the target mother pigs, the two litters were selected from three litters during the third birth among the expected births of May 31.

(6) Testing Sections (i) Test Section: To 8 piglets selected without bias from the 16 piglets, Formula Feed A and Formula Feed B were given according to the test plan shown in FIG. 1.

(ii) Control Section: To the remaining 8 piglets selected without bias from the 16 piglets, Stock Formula Feed A and Stock Formula Feed B were given according to the test plan shown in FIG. 1.

(7) Test Items (i) Body Weight Measurement

As shown in FIG. 1, all 16 piglets were measured individually for body weight at the start of the test, after 4 weeks, and after 8 weeks.

(ii) Feeding Amount of Feed

As shown in FIG. 1, the amount of feed given during the test period was measured for the test section and the control section and totaled each week.

(iii) Clinical Observation

Normal management was performed (if any abnormalities were recognized, the symptoms and treatments were recorded).

(iv) Fecal Test

As shown in FIG. 1, 20 g of feces was collected after 4 weeks had elapsed from the start of the test from 4 piglets randomly selected from the test section and 4 piglets randomly selected from the control section.

(v) Fecal Test Items (a) Fecal Characteristics Test

Test for moisture content and pH.

(b) Bacteria Test

Test for the number of aerobic bacteria, the number of anaerobic bacteria, the number of coliform bacilli, the number of *Bacteroides*, the number of *Bifidobacterium*, and the number of *Lactobacillus*.

(c) Decomposed Matter Test

Test for ammonia, p-cresol, 4-ethylphenol, indole, and skatole.

(vi) Test Organization

SMC Co., Ltd.: tests for pH, the number of aerobic bacteria, the number of anaerobic bacteria, the number of coliform bacilli, the number of *Bacteroides*, the number of *Bifidobacterium*, and the number of *Lactobacillus*.

Techno Suruga Lab Co., Ltd.: tests for moisture content, ammonia, p-cresol, 4-ethylphenol, indole, and skatole.

(8) Test Results

The tests results related to body weight are summarized in Table 2. The average body weight at the start of the test was 8.1 Kg/piglet in the test section, and 7.9 Kg/piglet in the control section. The average body weight at the end of the test after 8 weeks had elapsed was 47.5 Kg/piglet in the test section and 44.8 Kg/piglet in the control section. Thus, it is recognized that the piglets in the test section exhibited remarkable growth compared to the piglets of the control section.

The average daily body weight gain, which is the amount of body weight gain per piglet per day during the 8-week test period, was 0.703 Kg/piglet/day in the test section, and 0.658 Kg/piglet/day in the control section. Meanwhile, the average daily feed amount, which is the amount of feed consumed per piglet per day, was 1.319 Kg/piglet/day in the test section, and 1.211 Kg/piglet/day in the control section. Therein, upon calculating a feed demand rate, the feed demand rate was 1.876 in the test section, and 1.840 in the control section. The feed demand rate is calculated using the following Equation 1.

$$\text{feed demand rate} = \text{average daily feed amount} / \text{average daily body weight gain} \quad \text{(Eq. 1)}$$

The feed demand rate was higher in the test section than in the control section, and no feed reduction effects were observed during the piglet period of around 9 weeks after weaning. This result is believed to have occurred because the piglets of the test section were growing with extremely good health, and thus the amount of exercise of these piglets was increased. Further, it is believed that the basic physical strength of the piglets in the test section improved due to the increase in exercise, and this is presumed to lead to a decrease in the subsequent feed demand rate.

Table 3 shows the results upon measuring changes in the body weight of the piglets in the test section and the control section at the start of the test, after 4 weeks, and after 8 weeks, and calculating average values and standard deviations (the square root of the unbiased variance) for the test section and the control section. Table 4 shows the body weight gain (Kg/piglet), which is the amount of increase in body weight, during the periods of from the start of the test to after 4 weeks, from after 4 weeks to after 8 weeks, and from the start of the test to after 8 weeks, and also shows the daily body weight gain (Kg/piglet/day) during the above periods, and further shows average values and standard deviations of the body weight gain (Kg/piglet) and daily body weight gain (Kg/piglet/day).

Table 5 summarizes the average values and standard deviations of the body weight shown in Table 3 and the average values and standard deviations of the daily body weight gain shown in Table 4, and a t-test was performed for the difference in the average values between the test section and the control section. It is understood that a smaller p-value indicates a more significant difference between the two average values. For example, if the p-value is 0.05 or less, the significance is 5%, and this has traditionally indicated that a significant difference exists between the two average values.

In Table 5, with regard to the average body weight at the start of the test of 8.1 Kg/piglet in the test section and 7.9 Kg/piglet in the control section, the p-value is 0.682, and thus it can be said there is almost no significant difference in the average body weight between the test section and the control section. In other words, it can be understood that the piglets were selected without bias at the beginning of the test. In contrast, the p-value after 4 weeks is 0.126, and the p-value after 8 weeks is 0.232, and thus, although 5% significance was not reached, it can be understood that a significant difference in the average body weight is developing between the test section and the control section along with the passage of time.

Figure 2:
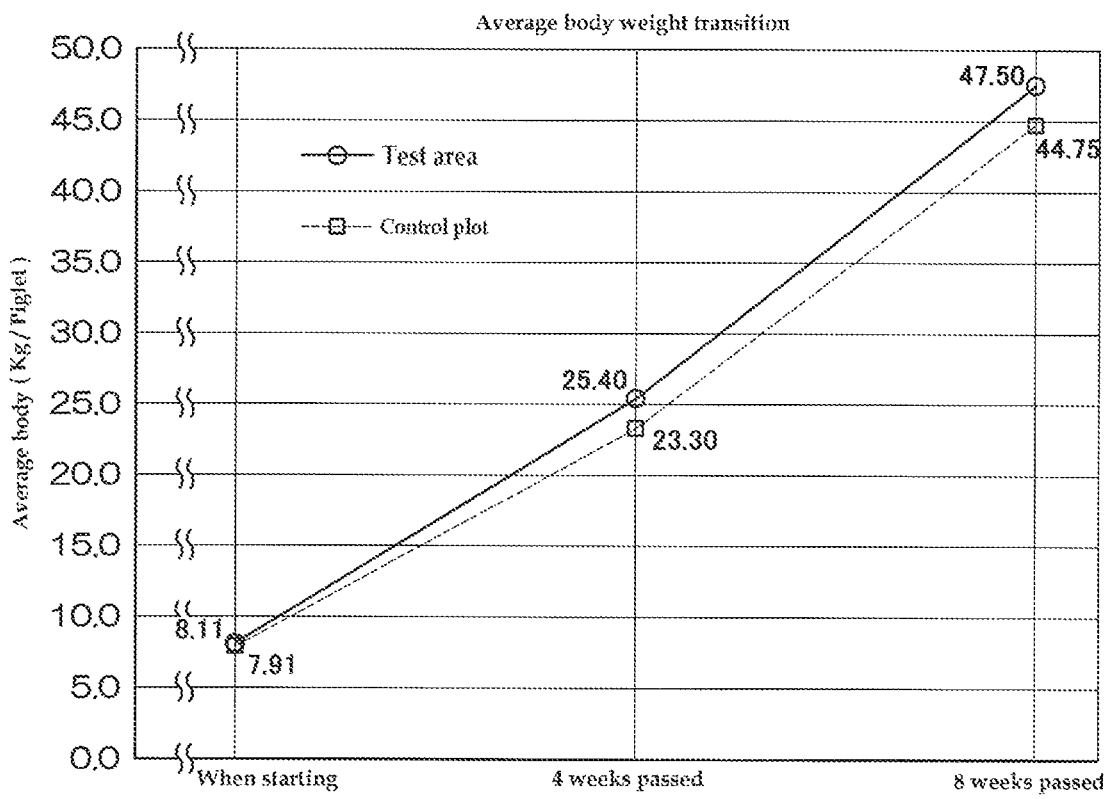
FIG. 2 is a graph illustrating test results related to changes in the average body weight of piglets of a test section which used the formula feed for raising pigs and piglets of a control section which used the stock formula feed.

Changes in the average body weight are shown in the graph of FIG. 2. From FIG. 2, it can be understood that the difference in the average body weight between the test section and the control section is increasing with the passage of time.

Meanwhile, with regard to the average daily body weight gain shown in Table 5, the p-value reached the numerical value of 0.095 for the test section and the control section during the period from the start of the test to after 4 weeks. Although 5% significance was not reached, it can be determined that the average daily body weight gain clearly increased more in the test section as compared to the control section. Further, the p-value for the average daily body weight gain in the period from after 4 weeks to after 8 weeks increased to 0.597, and thus a remarkable significance in the difference of the average values was no longer observed in this period. In addition, the p-value for the entire period from the start of the test to after 8 weeks is 0.223.

Figure 3:
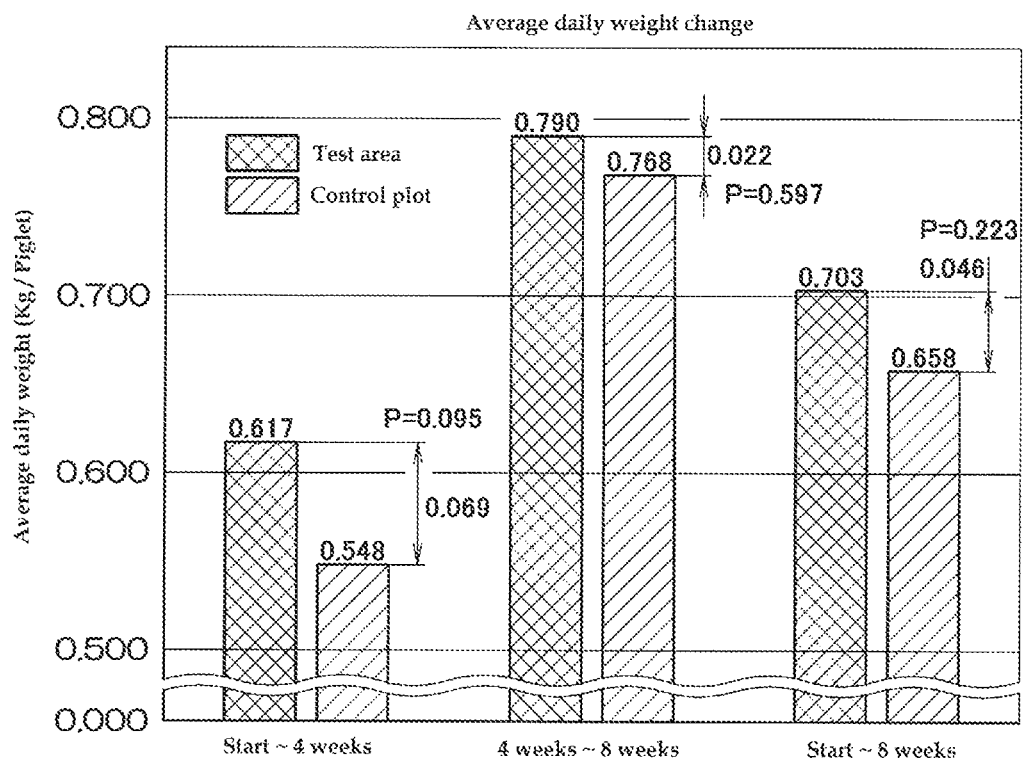
FIG. 3 is a graph illustrating test results related to changes in the average daily body weight gain of the piglets of the test section which used the formula feed for raising pigs and the piglets of the control section which used the stock formula feed.

The average daily body weight gain during the period from the start of the test to after 4 weeks, the period from after 4 weeks to after 8 weeks, and the entire period from the start of the test to after 8 weeks is graphed in FIG. 3 on the basis of Table 5. In FIG. 3, a considerable difference appears in the average values between the test section and the control section during the period from the start of the test to after 4 weeks, and it can be sensuously understood that this difference is significant.

Tables 6 and 7 show the results upon calculating the average values and standard deviations of the body weight, body weight gain, and daily body weight gain for the piglets which had initial body weight of less than 8.5 Kg at the start of the test (test section: 5 piglets; control section: 5 piglets) shown in Table 3. Table 8 shows the results upon performing a t-test based on the above-mentioned average values and standard deviations, etc.

As shown in Table 8, it can be understood that the piglets which had initial body weight of less than 8.5 Kg exhibited similar tendencies to the case in which all piglets were evaluated as shown in Table 5. However, the difference in the average values between the test section and the control section increased for the piglets of less than 8.5 Kg, and the p-value decreased. In other words, it can be understood that the effect of body weight increase achieved by the konnyaku fly powder is greater in the piglets of smaller body weights, and the significant difference was also more prominent in the piglets of smaller body weights.

Figure 4:
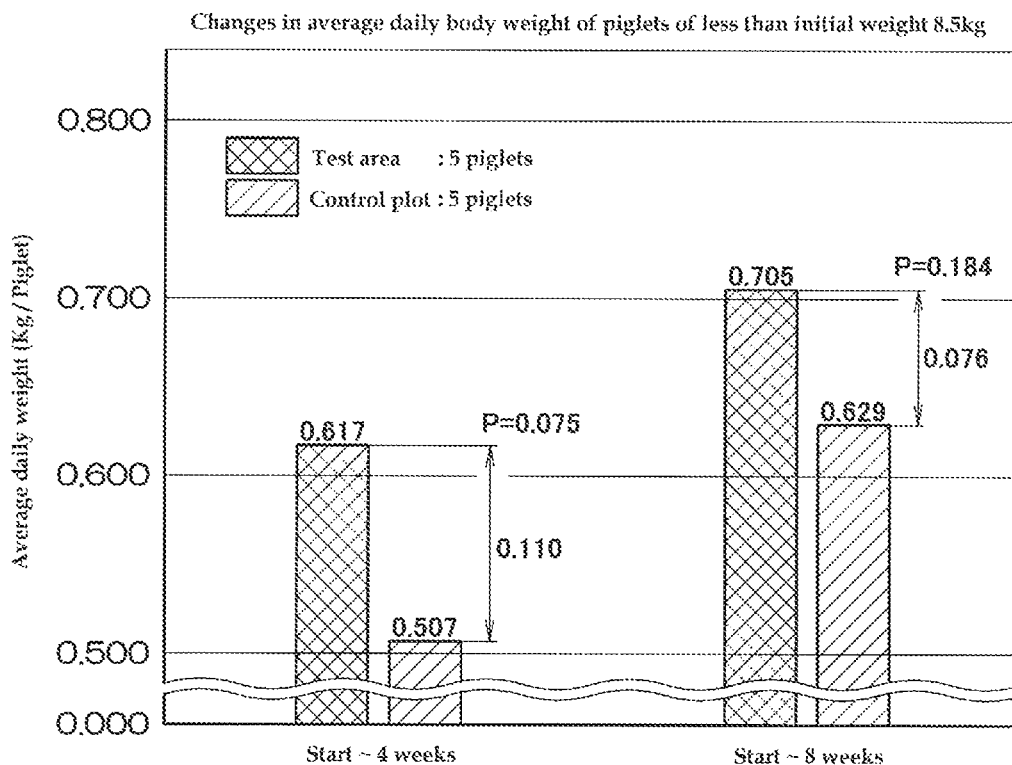
FIG. 4 is a graph illustrating test results related to changes in the average daily body weight gain for piglets which had initial body weight of less than 8.5 Kg among the piglets of the test section which used the formula feed for raising pigs and the piglets of the control section which used the stock formula feed.

FIG. 4 is a graph of the average daily body weight gain in the period from the start of the test to after 4 weeks and in the entire period from the start of the test to after 8 weeks shown in Table 8. Compared to FIG. 3 which is an evaluation of all of the piglets, it can be seen that the average daily body weight gain is increasing between the test section and the control section, and that the p-value is decreasing.

Table 9 summarizes the data regarding the average daily feed amount, which is the amount of feed consumed per piglet per day, for the period from the start of the test to after 4 weeks, the period from after 4 weeks to after 8 weeks, and the entire period from the start of the test to after 8 weeks. The average daily feed amount is greater in the test section compared to the control section in all of the above periods.

Table 10 summarizes the data regarding the feed demand rate for the period from the start of the test to after 4 weeks, the period from after 4 weeks to after 8 weeks, and the entire period from the start of the test to after 8 weeks. The feed demand rate for each period was calculated by dividing the average daily feed amount for each period given in Table 9 by the average daily body weight gain corresponding to each period given in Table 5.

The feed demand rate was lower in the test section than the control section during the period from the start to the $4^{th}$ week, but was higher in the test section than the control section during the period from the 4th week to the $8^{th}$ week, and as mentioned above, the feed demand rate was higher in the test section than the control section during the entire period from the test start to the $8^{th}$ week.

Table 11 indicates the average values and standard deviations of the number of each bacterium obtained by the fecal bacteria test conducted after 4 weeks. Table 12 shows the results upon performing a t-test based on the above-mentioned average values and standard deviations, etc. The average numbers of each bacteria given in Table 11 and Table 12 are graphed in FIG. 5.

Figure 5:
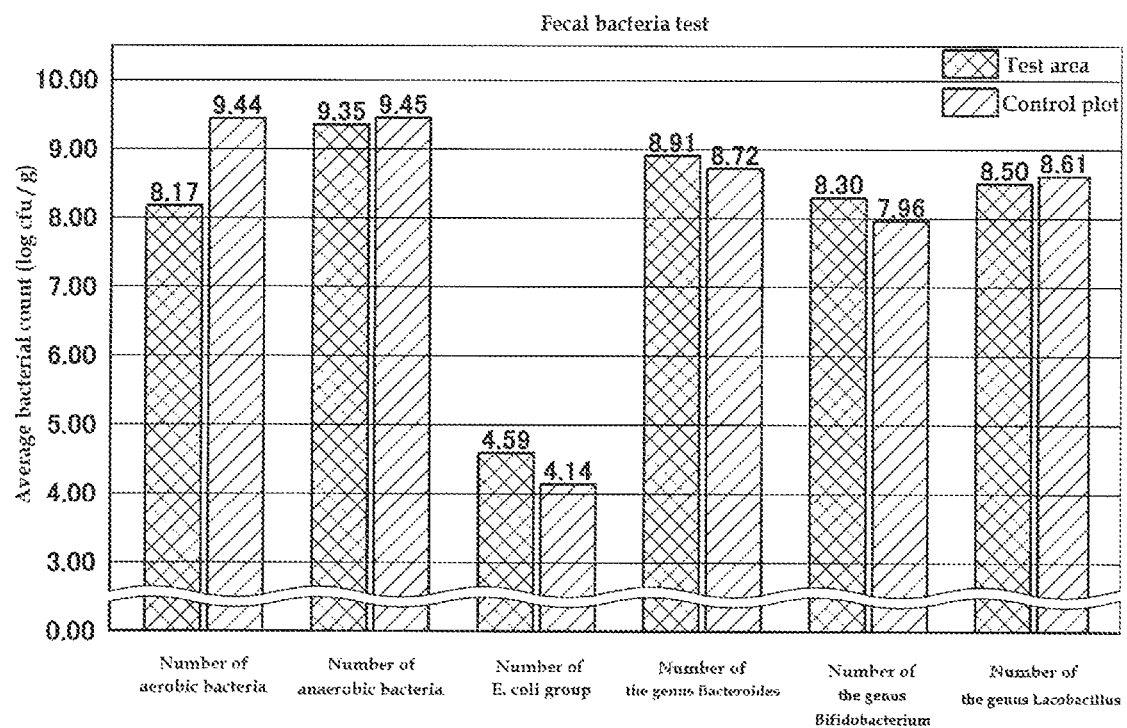
FIG. 5 is a graph illustrating test results of a fecal bacteria test for the piglets of the test section which used the formula feed for raising pigs and the piglets of the control section which used the stock formula feed.
Figure 6A:
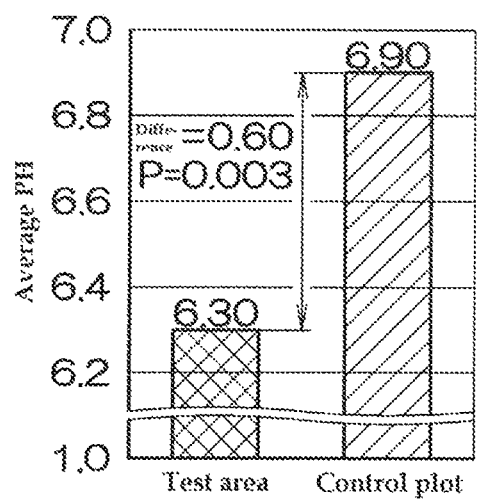
FIGS. 6A-6G are graphs illustrating test results related to fecal characteristics and decomposed matter in feces for the piglets of the test section which used the formula feed for raising pigs and the piglets of the control section which used the stock formula feed.
Figure 6B:
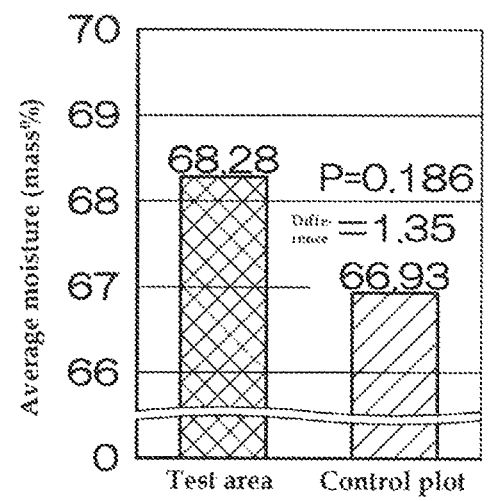
Figure 6C:
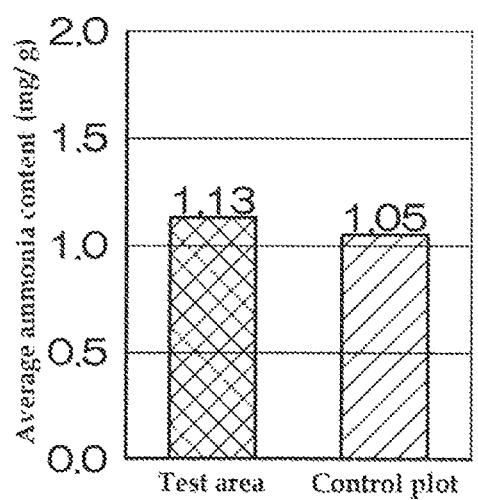
Figure 6D:
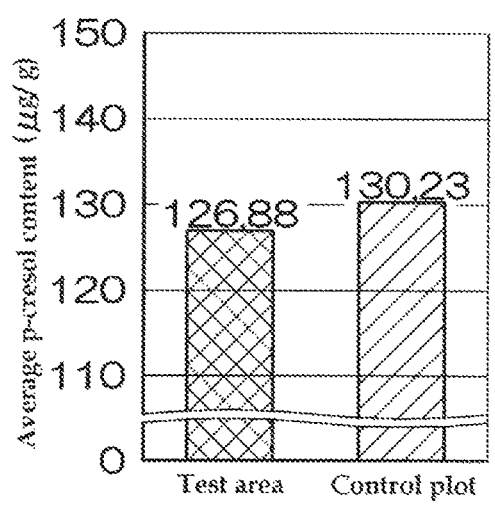
Figure 6E:
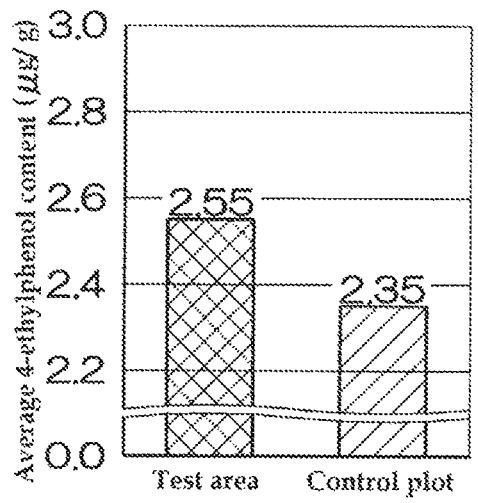
Figure 6F:
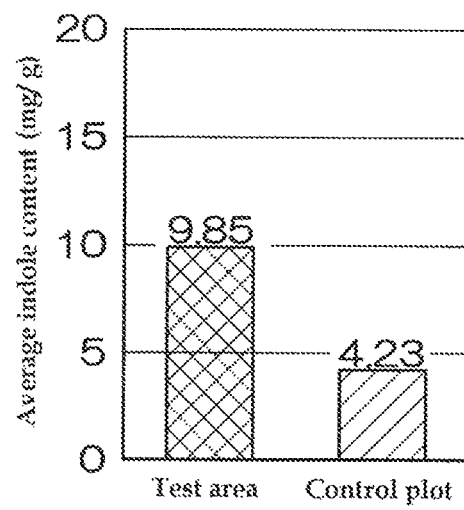
Figure 6G:
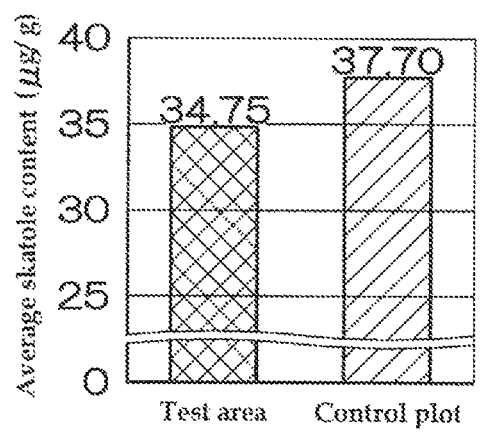

As shown in Table 12 and FIG. 5, the number of aerobic bacteria and anaerobic bacteria, which are bad bacteria, was smaller in the test section than in the control section. In particular, the p-value for aerobic bacteria was 0.034, and thus 5% significance was reached. Meanwhile, the number of coliform bacilli was higher in the test section than in the control section. However, as shown in FIG. 5, the absolute number of coliform bacilli was smaller compared to the other bacteria, and thus the above result is not believed to be a problem.

On the other hand, the number of *Bacteroides* and *Bifidobacterium*, which are good bacteria, was greater in the test section than in the control section. However, the number of *Lactobacillus* was greater in the test section than in the control section. The p-value for the number of *Bacteroides*, the number of *Bifidobacterium*, and the number of *Lactobacillus* is 0.651, 0.505, and 0.881 respectively. Therefore, no remarkable significance can be recognized in the average values between the test section and the control section for the good bacteria. However, the p-value for the number of *Bifidobacterium* was the smallest at 0.505, and thus there is a high probability that the number of *Bifidobacterium* is greater in the test section than in the control section.

Table 13 shows the average values and standard deviations of the characteristics and component amounts obtained by the fecal characteristics test conducted after 4 weeks, and Table 14 shows the results upon performing a t-test based on the above-mentioned average values and standard deviations, etc. The average values of each characteristic and the component amounts given in Table 13 and Table 14 are graphed in FIG. 6.

As shown in Table 14, the difference in the average values for the pH was 0.60, and the p-value is 0.003 (0.5% significance). In other words, it can be said that the average value of 6.30 for the pH in the test section exhibits a clear significant difference from the average value of 6.90 for the pH in the control section. Therefore, there is an extremely high probability that the test section is more slightly acidic than the control section.

As shown in Table 14, the difference in the average values for the moisture was 1.35, and the p-value was 0.186. While 5% significance was not reached, it is recognized that this difference exhibits relatively high significance. Therefore, it can be said that the moisture tends to be higher in the test section compared to the control section.

As shown in Table 14 and FIG. 6, with regard to ammonia, p-cresol, 4-ethylphenol, indole, and skatole, which correspond to decomposed matter, there were cases in which the average values were higher in the test section compared to the control section as well as cases in which the average values were lower in the test section compared to the control section. Thus, no clear difference was observed between the test section and the control section.

TABLE 2

Summary of test results for weight relationship

|  | Test area | Control plot | Difference |
|---|---|---|---|
| The Number of piglets | 8 | 8 | — |
| The test days | 56 | 56 | — |
| Number of piglet used for the test | 448 | 448 | — |
| The sum total weight at starting (Kg) | 64.9 | 63.3 | 1.6 |

TABLE 2-continued

Summary of test results for weight relationship

|  | Test area | Control plot | Difference |
|---|---|---|---|
| The average weight at starting (Kg/Pig) | 8.1 | 7.9 | 0.2 |
| The sum total weight at ending (Kg) | 380.0 | 358.0 | 22.0 |
| The average weight at ending (Kg/Piglets) | 47.5 | 44.8 | 2.7 |
| Total of the gain in weight (Kg) | 315.1 | 294.7 | 20.4 |
| Average of the daily gain in weight (Kg/Piglets) | 0.703 | 0.658 | 0.046 |
| Total feed volume (Kg) | 591.0 | 542.5 | 48.5 |
| Average of the daily gain to feeds (Kg/Piglets) | 1.319 | 1.211 | 0.108 |
| Feed Request Ratio | 1.876 | 1.840 | 0.035 |

TABLE 3

Weight change of pigs

|  |  |  |  | Weight (Kg) | | |
|---|---|---|---|---|---|---|
|  | Individual number | Sex | Start | 4 week lapse | 8 week lapse |
| Test area | 566 | ♀ | 6.8 | 25.0 | 50.0 |
|  | 571 | ♂ | 9.0 | 25.0 | 46.0 |
|  | 572 | ♂ | 8.3 | 27.0 | 51.0 |
|  | 573 | ♂ | 8.3 | 27.0 | 47.0 |
|  | 594 | ♀ | 8.0 | 21.0 | 39.0 |
|  | 595 | ♀ | 8.5 | 26.0 | 49.0 |
|  | 596 | ♀ | 8.8 | 27.0 | 49.0 |
|  | 598 | ♀ | 7.2 | 25.0 | 49.0 |
|  | Total |  | 64.9 | 203.0 | 380.0 |
|  | Average |  | 8.1 | 25.4 | 47.5 |
|  | Standard deviation |  | 0.761 | 1.996 | 3.778 |
| Control plot | 565 | ♀ | 8.5 | 26.0 | 47.0 |
|  | 568 | ♀ | 9.0 | 26.0 | 48.0 |
|  | 574 | ♂ | 8.2 | 26.0 | 50.0 |
|  | 576 | ♂ | 5.6 | 20.0 | 38.0 |
|  | 592 | ♀ | 7.5 | 21.0 | 40.0 |
|  | 593 | ♀ | 8.0 | 22.0 | 45.0 |
|  | 600 | ♀ | 8.8 | 26.0 | 50.0 |
|  | 601 | ♂ | 7.7 | 19.0 | 40.0 |
|  | Total |  | 63.3 | 186.0 | 358.0 |
|  | Average |  | 7.9 | 23.3 | 44.8 |
|  | Standard deviation |  | 1.067 | 3.059 | 4.803 |

TABLE 4

Changes in weight gain and daily weight gain

|  |  |  | Weight gain (Kg) | | | Daily weight gain (Kg/Day) | | |
|---|---|---|---|---|---|---|---|---|
|  | Individual number | Sex | Start~4 week lapse | 4 week lapse~8 week lapse | Start~8 week lapse | Start~4 week lapse | 4 week lapse~8 week lapse | Start~8 week lapse |
| Test area | 566 | ♀ | 18.2 | 25.0 | 43.2 | 0.650 | 0.893 | 0.771 |
|  | 571 | ♂ | 16.0 | 21.0 | 37.0 | 0.571 | 0.750 | 0.661 |
|  | 572 | ♂ | 18.7 | 24.0 | 42.7 | 0.668 | 0.857 | 0.763 |
|  | 573 | ♂ | 18.7 | 20.0 | 38.7 | 0.668 | 0.714 | 0.691 |
|  | 594 | ♀ | 13.0 | 18.0 | 31.0 | 0.464 | 0.643 | 0.554 |
|  | 595 | ♀ | 17.5 | 23.0 | 40.5 | 0.625 | 0.821 | 0.723 |
|  | 596 | ♀ | 18.2 | 22.0 | 40.2 | 0.650 | 0.786 | 0.718 |
|  | 598 | ♀ | 17.8 | 24.0 | 41.8 | 0.636 | 0.857 | 0.746 |
|  | Total |  | 138.1 | 177.0 | 315.1 | 4.932 | 6.321 | 5.627 |
|  | Average |  | 17.3 | 22.1 | 39.4 | 0.617 | 0.790 | 0.703 |
|  | Standard deviation |  | 1.93 | 2.36 | 3.96 | 0.0690 | 0.0841 | 0.0705 |
| Control plot | 565 | ♀ | 17.5 | 21.0 | 38.5 | 0.625 | 0.750 | 0.688 |
|  | 568 | ♀ | 17.0 | 22.0 | 39.0 | 0.607 | 0.786 | 0.696 |
|  | 574 | ♂ | 17.8 | 24.0 | 41.8 | 0.636 | 0.857 | 0.746 |
|  | 576 | ♂ | 14.4 | 18.0 | 32.4 | 0.514 | 0.643 | 0.579 |
|  | 592 | ♀ | 13.5 | 19.0 | 32.5 | 0.482 | 0.679 | 0.580 |
|  | 593 | ♀ | 14.0 | 23.0 | 37.0 | 0.500 | 0.821 | 0.661 |
|  | 600 | ♀ | 17.2 | 24.0 | 41.2 | 0.614 | 0.857 | 0.736 |
|  | 601 | ♂ | 11.3 | 21.0 | 32.3 | 0.404 | 0.750 | 0.577 |
|  | Total |  | 122.7 | 172 | 294.7 | 4.382 | 6.143 | 5.263 |
|  | Average |  | 15.3 | 21.5 | 36.8 | 0.548 | 0.768 | 0.658 |
|  | Standard deviation |  | 2.37 | 2.20 | 3.97 | 0.0846 | 0.0785 | 0.0708 |

TABLE 5

The t test on growth promotion of all pigs

|  |  | Test area | | Control plot | | | | |
|---|---|---|---|---|---|---|---|---|
|  |  | Average | Standard deviation | Average | Standard deviation | Average difference | t vaule | p vaule |
| Average weight (Kg/Pig) | Start | 8.1 | 0.761 | 7.9 | 1.067 | 0.2 | 0.418 | 0.682 |
|  | 4 week lapse | 25.4 | 1.996 | 23.3 | 3.059 | 2.1 | 1.626 | 0.126 |
|  | 8 week lapse | 47.5 | 3.778 | 44.8 | 4.803 | 2.8 | 1.250 | 0.232 |
| Average of the daily gain in weight (Kg/Pig) | Start~4 week lapse | 0.617 | 0.0690 | 0.548 | 0.0846 | 0.069 | 1.788 | 0.095 |
|  | 4 week lapse~8 week lapse | 0.790 | 0.0841 | 0.768 | 0.0785 | 0.022 | 0.541 | 0.597 |
|  | Start~8 week lapse | 0.703 | 0.0705 | 0.658 | 0.0708 | 0.045 | 1.274 | 0.223 |

TABLE 6

Changes in weight of piglets with initial weight less than 8.5 kg

|  | Individual number | Sex | Weight (Kg) | | |
|---|---|---|---|---|---|
|  |  |  | Start | 4 week lapse | 8 week lapse |
| Test area | 566 | ♀ | 6.8 | 25.0 | 50.0 |
|  | ~~571~~ | ♂ | ~~9.0~~ | ~~25.0~~ | ~~46.0~~ |
|  | 572 | ♂ | 8.3 | 27.0 | 51.0 |
|  | 573 | ♂ | 8.3 | 27.0 | 47.0 |
|  | 594 | ♀ | 8.0 | 21.0 | 39.0 |
|  | ~~595~~ | ♀ | ~~8.5~~ | ~~26.0~~ | ~~49.0~~ |
|  | ~~596~~ | ♀ | ~~8.8~~ | ~~27.0~~ | ~~49.0~~ |
|  | 598 | ♀ | 7.2 | 25.0 | 49.0 |
|  | Total |  | 38.6 | 125.0 | 236.0 |
|  | Average |  | 7.7 | 25.0 | 47.2 |
|  | Standard deviation |  | 0.683 | 2.449 | 4.817 |
| Control plot | ~~565~~ | ♀ | ~~8.5~~ | ~~26.0~~ | ~~47.0~~ |
|  | ~~568~~ | ♀ | ~~9.0~~ | ~~26.0~~ | ~~48.0~~ |
|  | 574 | ♂ | 8.2 | 26.0 | 50.0 |
|  | 576 | ♂ | 5.6 | 20.0 | 38.0 |
|  | 592 | ♀ | 7.5 | 21.0 | 40.0 |
|  | 593 | ♀ | 8.0 | 22.0 | 45.0 |
|  | ~~600~~ | ♀ | ~~8.8~~ | ~~26.0~~ | ~~50.0~~ |
|  | 601 | ♂ | 7.7 | 19.0 | 40.0 |
|  | Total |  | 37.0 | 108.0 | 213.0 |
|  | Average |  | 7.4 | 21.6 | 42.6 |
|  | Standard deviation |  | 1.042 | 2.702 | 4.879 |

TABLE 7

Changes in weight gain and daily weight of piglets of less than initial weight

|  | Individual number | Sex | Weight gain (Kg) | | | Daily weight gain (Kg/Day) | | |
|---|---|---|---|---|---|---|---|---|
|  |  |  | Start ~ 4 week lapse | 4 week lapse ~ 8 week lapse | Start ~ 8 week lapse | Start ~ 4 week lapse | 4 week lapse ~ 8 week lapse | Start ~ 8 week lapse |
| Test area | 566 | ♀ | 18.2 | 25.0 | 43.2 | 0.650 | 0.893 | 0.771 |
|  | ~~571~~ | ♂ | ~~16.0~~ | ~~21.0~~ | ~~37.0~~ | ~~0.571~~ | ~~0.750~~ | ~~0.661~~ |
|  | 572 | ♂ | 18.7 | 24.0 | 42.7 | 0.668 | 0.857 | 0.763 |
|  | 573 | ♂ | 18.7 | 20.0 | 38.7 | 0.668 | 0.714 | 0.691 |
|  | 594 | ♀ | 13.0 | 18.0 | 31.0 | 0.464 | 0.643 | 0.554 |
|  | ~~595~~ | ♀ | ~~17.5~~ | ~~23.0~~ | ~~40.5~~ | ~~0.625~~ | ~~0.821~~ | ~~0.723~~ |
|  | ~~596~~ | ♀ | ~~18.2~~ | ~~22.0~~ | ~~40.2~~ | ~~0.650~~ | ~~0.786~~ | ~~0.718~~ |
|  | 598 | ♀ | 17.8 | 24.0 | 41.8 | 0.636 | 0.857 | 0.746 |
|  | Total |  | 86.4 | 111.0 | 197.4 | 3.086 | 3.964 | 3.525 |
|  | Average |  | 17.3 | 22.2 | 39.5 | 0.617 | 0.793 | 0.705 |
|  | Standard deviation |  | 2.42 | 3.03 | 5.05 | 0.0867 | 0.1083 | 0.0900 |
| Control plot | ~~565~~ | ♀ | ~~17.5~~ | ~~21.0~~ | ~~38.5~~ | ~~0.625~~ | ~~0.750~~ | ~~0.688~~ |
|  | ~~568~~ | ♀ | ~~17.0~~ | ~~22.0~~ | ~~39.0~~ | ~~0.607~~ | ~~0.786~~ | ~~0.696~~ |
|  | 574 | ♂ | 17.8 | 24.0 | 41.8 | 0.636 | 0.857 | 0.746 |
|  | 576 | ♂ | 14.4 | 18.0 | 32.4 | 0.514 | 0.643 | 0.579 |
|  | 592 | ♀ | 13.5 | 19.0 | 32.5 | 0.482 | 0.679 | 0.580 |
|  | 593 | ♀ | 14.0 | 23.0 | 37.0 | 0.500 | 0.821 | 0.661 |
|  | ~~600~~ | ♀ | ~~17.2~~ | ~~24.0~~ | ~~41.2~~ | ~~0.614~~ | ~~0.857~~ | ~~0.736~~ |
|  | 601 | ♂ | 11.3 | 21.0 | 32.3 | 0.404 | 0.750 | 0.577 |
|  | Total |  | 71.0 | 105.0 | 176.0 | 2.536 | 3.750 | 3.143 |
|  | Average |  | 14.2 | 21.0 | 35.2 | 0.507 | 0.750 | 0.629 |
|  | Standard deviation |  | 2.34 | 2.55 | 4.19 | 0.0836 | 0.0908 | 0.0747 |

TABLE 8

The t test on developmental growth of piglets of less than initial weight 8.5 kg

|  |  | Test area | | Control plot | | | | |
|---|---|---|---|---|---|---|---|---|
|  |  | Average | Standard deviation | Average | Standard deviation | Average difference | t vaule | p vaule |
| Average weight (Kg/Pig) | Start | 7.7 | 0.683 | 7.4 | 1.042 | 0.3 | 0.538 | 0.605 |
|  | 4 week lapse | 25.0 | 2.449 | 21.6 | 2.702 | 3.4 | 2.085 | 0.071 |
|  | 8 week lapse | 47.2 | 4.817 | 42.6 | 4.879 | 4.6 | 1.500 | 0.172 |
| Average of the daily gain in weight (Kg/Pig) | Start~4 week lapse | 0.617 | 0.0867 | 0.507 | 0.0836 | 0.110 | 2.042 | 0.075 |
|  | 4 week lapse~8 week lapse | 0.793 | 0.1083 | 0.750 | 0.0908 | 0.043 | 0.680 | 0.515 |
|  | Start~8 week lapse | 0.705 | 0.0900 | 0.629 | 0.0747 | 0.076 | 1.453 | 0.184 |

TABLE 9

| Average daily feed volume (Kg/Pig) | | | |
| --- | --- | --- | --- |
| | Test area | Control plot | Difference |
| Start~4 week lapse | 0.902 | 0.824 | 0.078 |
| 4 week lapse~8 week lapse | 1.737 | 1.598 | 0.139 |
| Start~8 week lapse | 1.319 | 1.211 | 0.108 |

TABLE 10

| Feed conversion rate | | | |
| --- | --- | --- | --- |
| | Test area | Control plot | Difference |
| Start~4 week lapse | 1.46 | 1.50 | −0.04 |
| 4 week lapse~8 week lapse | 2.20 | 2.08 | 0.12 |
| Start~8 week lapse | 1.88 | 1.84 | 0.04 |

TABLE 11

| | | | | | | | | (log cfu/g) |
| --- | --- | --- | --- | --- | --- | --- | --- | --- |
| | | Individual number | Sex | Number of aerobic bacteria | Number of anaerobic bacteria | Number of *E. coli* groups | Number of the genus *Bacteroides* | Number of the genus *Bifidobacterium* | Number of the genus *Lacobacillus* |
| Test area | | 566 | ♀ | 8.71 | 9.56 | 5.72 | 8.64 | 7.90 | 8.45 |
| | | 571 | ♂ | 9.00 | 9.83 | 5.98 | 9.63 | 8.69 | 8.28 |
| | | 572 | ♂ | — | — | — | — | — | — |
| | | 573 | ♂ | — | — | — | — | — | — |
| | | 594 | ♀ | — | — | — | — | — | — |
| | | 595 | ♀ | 6.90 | 9.08 | 3.20 | 8.60 | 7.83 | 7.90 |
| | | 596 | ♀ | 8.08 | 8.92 | 3.45 | 8.78 | 8.78 | 9.38 |
| | | 598 | ♀ | — | — | — | — | — | — |
| | Total | | | 32.69 | 37.39 | 18.35 | 35.65 | 33.20 | 34.01 |
| | Average | | | 8.17 | 9.35 | 4.59 | 8.91 | 8.30 | 8.50 |
| | Standard deviation | | | 0.931 | 0.421 | 1.465 | 0.485 | 0.504 | 0.629 |
| Control plot | | 565 | ♀ | — | — | — | — | — | — |
| | | 568 | ♀ | — | — | — | — | — | — |
| | | 574 | ♂ | 9.45 | 9.30 | 5.26 | 9.60 | 8.60 | 9.20 |
| | | 576 | ♂ | 9.43 | 9.20 | 2.90 | 8.60 | 8.60 | 10.08 |
| | | 592 | ♀ | — | — | — | — | — | — |
| | | 593 | ♀ | — | — | — | — | — | — |
| | | 600 | ♀ | 9.45 | 11.08 | 2.90 | 8.60 | 6.90 | 7.30 |
| | | 601 | ♂ | 9.43 | 8.23 | 5.51 | 8.08 | 7.74 | 7.86 |
| | Total | | | 37.76 | 37.81 | 16.57 | 34.88 | 31.84 | 34.44 |
| | Average | | | 9.44 | 9.45 | 4.14 | 8.72 | 7.96 | 8.61 |
| | Standard deviation | | | 0.012 | 1.187 | 1.438 | 0.636 | 0.815 | 1.263 |

Detection limit: $4.0 \times 10^2$ cfu/g

TABLE 12

| | | | | | | | (log cfu/g) |
| --- | --- | --- | --- | --- | --- | --- | --- |
| | Test area | | Control plot | | | | |
| | Average | Standard deviation | Average | Standard deviation | Average difference | t vaule | p vaule |
| Number of aerobic bacteria | 8.17 | 0.931 | 9.44 | 0.012 | 1.27 | 2.728 | 0.034 |
| Number of anaerobic bacteria | 9.35 | 0.421 | 9.45 | 1.187 | 0.10 | 0.159 | 0.879 |
| Number of *E. coli* group | 4.59 | 1.465 | 4.14 | 1.438 | 0.45 | 0.438 | 0.676 |
| Number of the genus *Bacteroides* | 8.91 | 0.485 | 8.72 | 0.636 | 0.19 | 0.475 | 0.651 |
| Number of the genus *Bifidobacterium* | 8.30 | 0.504 | 7.96 | 0.815 | 0.34 | 0.710 | 0.505 |
| Number of the genus *Lacobacillus* | 8.50 | 0.629 | 8.61 | 1.263 | 0.11 | 0.156 | 0.881 |

TABLE 13

Inspection of feces component

| | Individual number | Sex | PH | Moisture (Mass %) | Ammonia (mg/g) | P-cresol (µg/g) | 4-ethylphenol (µg/g) | Indole (µg/g) | Skatole (µg/g) |
|---|---|---|---|---|---|---|---|---|---|
| Test area | 566 | ♀ | 6.30 | 68.10 | 1.48 | 157.00 | 1.30 | 34.70 | 22.90 |
| | 571 | ♂ | 6.00 | 68.90 | 0.89 | 102.20 | 1.50 | 0.80 | 32.40 |
| | 572 | ♂ | — | — | — | — | — | — | — |
| | 573 | ♂ | — | — | — | — | — | — | — |
| | 594 | ♀ | — | — | — | — | — | — | — |
| | 595 | ♀ | 6.30 | 66.60 | 1.29 | 151.30 | 3.20 | 2.50 | 54.90 |
| | 596 | ♀ | 6.60 | 69.50 | 0.86 | 97.00 | 4.20 | 1.40 | 28.80 |
| | 598 | ♀ | — | — | — | — | — | — | — |
| | Total | | 25.20 | 273.10 | 4.52 | 507.50 | 10.20 | 39.40 | 139.00 |
| | Average | | 6.30 | 68.28 | 1.13 | 126.88 | 2.55 | 9.85 | 34.75 |
| | Standard deviation | | 0.245 | 1.255 | 0.305 | 31.652 | 1.392 | 16.582 | 13.992 |
| Control plot | 565 | ♀ | — | — | — | — | — | — | — |
| | 568 | ♀ | — | — | — | — | — | — | — |
| | 574 | ♂ | 6.90 | 67.20 | 0.83 | 94.50 | 1.20 | 3.30 | 21.20 |
| | 576 | ♂ | 6.90 | 67.20 | 1.00 | 134.90 | 3.20 | 10.10 | 26.20 |
| | 592 | ♀ | — | — | — | — | — | — | — |
| | 593 | ♀ | — | — | — | — | — | — | — |
| | 600 | ♀ | 6.90 | 68.20 | 1.12 | 102.40 | 4.50 | 2.00 | 44.80 |
| | 601 | ♂ | 6.90 | 65.10 | 1.25 | 189.10 | 0.50 | 1.50 | 58.60 |
| | Total | | 27.6 | 267.70 | 4.20 | 520.90 | 9.40 | 16.90 | 150.80 |
| | Average | | 6.90 | 66.93 | 1.05 | 130.23 | 2.35 | 4.23 | 37.70 |
| | Standard deviation | | 0.000 | 1.305 | 0.179 | 42.968 | 1.834 | 3.989 | 17.241 |

TABLE 14

The t test with feces component

| | Test area | | Control plot | | Average difference | t vaule | p vaule |
|---|---|---|---|---|---|---|---|
| | Average | Standard deviation | Average | Standard deviation | | | |
| PH | 6.30 | 0.245 | 6.90 | 0.000 | 0.60 | 4.898 | 0.003 |
| Moisture (Mass %) | 68.28 | 1.255 | 66.93 | 1.305 | 1.35 | 1.491 | 0.186 |
| Ammonia (mg/g) | 1.13 | 0.305 | 1.05 | 0.179 | 0.08 | 0.452 | 0.667 |
| P-cresol (µg/g) | 126.88 | 31.652 | 130.23 | 42.968 | 3.35 | 0.126 | 0.904 |
| 4-ethylphenol (µg/g) | 2.55 | 1.392 | 2.35 | 1.834 | 0.20 | 0.174 | 0.868 |
| Indole (µg/g) | 9.85 | 16.582 | 4.23 | 3.989 | 5.62 | 0.659 | 0.534 |
| Skatole (µg/g) | 34.75 | 13.992 | 37.70 | 17.241 | 2.95 | 0.266 | 0.799 |

(9) Observations Regarding Test Results

In the growth results for the piglets related to body weight, as shown in Table 5, the average daily body weight gain over the entire test period of 8 weeks was 0.703 Kg/piglet/day in the test section and 0.658 Kg/piglet/day in the control section. The difference therebetween is 0.045 Kg/piglet/day and the p-value is 0.223. Thus, although 5% significance could not be recognized, the growth body weight gain was better with a relatively high probability in the test section compared to the control section.

Further, in the growth results from the test start to after 4 weeks, as shown in Table 5, the average daily body weight gain was 0.617 Kg/piglet/day in the test section and 0.548 Kg/piglet/day in the control section. The difference therebetween is 0.069 Kg/piglet/day, and the p-value is 0.095 which indicates 10% significance. In addition, in the growth results from the test start to after 4 weeks for the piglets having an initial body weight of less than 8.5 Kg, as shown in Table 8, the average daily body weight gain was 0.617 Kg/piglet/day in the test section and 0.507 Kg/piglet day in the control section. The difference therebetween is 0.110 Kg/piglet/day, and the p-value is 0.075 which indicates that the significant difference is even more prominent. Therefore, it can be said that the konnyaku fly powder has a stronger effect of improving the growth body weight gain in the piglets of a smaller body weight.

Meanwhile, with regard to the feed supply rate, as shown in Tables 2 and 10, the value in the test section was higher than in the control section when considering the entire test period of 8 weeks. In other words, it can be determined that in the test section, an increase in body weight matching the increase in the amount of food ingested relative to the control section was not obtained. As a cause for this result, it is believed that in the test section, the amount of exercise characteristic of piglets increased along with the promotion of growth, and thus a portion of food was expended as exercise energy. Therefore, it can be anticipated that an increase in basic physical strength along with such exercise will lead to an increase in subsequent growth body weight gain, and as a result the feed supply rate over the entire growth period will decrease and the added value as premium meat will increase.

In the fecal bacteria test, as shown in Table 12 and FIG. 5, the number of *Bifidobacterium* was superior in the test section compared to the control section, and this is believed to be an effect of the konnyaku fly powder. Further, the average value of the pH of the feces in the test section became slightly acidic reaching 6.30, and this is believed to have occurred because of the production of acetic acid and lactic acid by *Bifidobacterium*.

As shown in Table 14, the average value of the pH in the feces was 6.30 in the test section and 6.90 in the control section. The difference therebetween is 0.60 and the p-value is 0.003, and thus 0.5% significance was recognized. This is presumed to be because organic acids were included in large amounts in the feces, which caused a decrease in the pH of the feces in the test section compared to the control section.

As shown in Table 14, the average value of the moisture in the feces was 68.28% by mass in the test section and 66.93% by mass in the control section. The difference therebetween is 1.35% by mass, and the p-value is 0.186. Although 10% significance was not reached, it is recognized that the difference is significant with a relatively high probability. It is believed that the bowel movements of the piglets in the test section were improved, and thus the moisture retained the intraintestinal environment in a good condition.

Given the above results, it is believed that adding the konnyaku fly powder to the formula feed brings about an increase in *Bifidobacterium* which in turn increases the amount of acetic acid and lactic acid leading to an improved intraintestinal environment, and as a result thereof, the amount of feed ingested increases and the growth body weight gain improves. In particular, in piglets of a small body weight, the effect of improving the growth body weight gain was greater, and thus it is believed that konnyaku fly powder is a necessary material for recent pig raising aimed at improving the results of breeding.

In the formula feed for raising pigs (Formula Feeds A and B) constituted as described above, 1% by mass of the konnyaku fly powder was added. As mentioned above, the konnyaku fly powder includes 18.4% by mass in HPLC ratio of glucomannan and 7.2% by mass of cellulose, which have a good influence on the intraintestinal environment. Therefore, the formula feed for raising pigs can improve the growth body weight gain, especially when given to piglets of a small body weight immediately after weaning, and can grow extremely healthy piglets with an improved basic physical strength due to increases in the amount of exercise. Accordingly, the formula feed for raising pigs can improve the feed supply rate over the entire period until shipment, and can increase the added value of the pork.

Further, in the actual test, the piglets in the test section which used the formula feed to which the konnyaku fly powder was added exhibited a good appetite and remarkable increases in body weight compared to the control section during the first 4 weeks (refer to Tables 5 and 8 and FIGS. 2, 3, and 5). Moreover, during the 4-week period from the $5^{th}$ week to the $8^{th}$ week as well, the body weight increase continued although it had slowed down slightly compared to the first 4 weeks (refer again to Tables 5 and 8 and FIGS. 2, 3, and 5). In addition, from FIG. 2, it can be understood that even after 8 weeks had elapsed, the piglets of the test section tended to be larger and gain more body weight compared to the piglets of the control section.

Considering the causes behind the body weight gain in the piglets of the test section, in the period after weaning in which the piglets are switched from weaning feed to regular formula feed, which is a particularly important period for the growth of piglets, it is necessary acclimate the stomach and bowels so as to decrease stress related to the physical condition as much as possible so that the piglets can freely grow and develop, and it is believed that the konnyaku fly powder plays an important role in achieving these goals.

By adding 1% by mass of the konnyaku powder to the formula feed, the cellulose and glucomannan, etc. included in the konnyaku fly powder enter the intestine, leading to increases in good bacteria such as *Bifidobacterium* which have a positive effect on the intraintestinal environment (refer to Table 12 and FIG. 5) and decreases in bad bacteria such as aerobic bacteria (refer again to Table 12 and FIG. 5). Further, *Bifidobacterium* causes an increase in lactic acid and acetic acid, which leads the pH in the intestine to become slightly acidic at around 6.30 (refer to Table 14 and FIG. 6(*a*)), and this can suppress the proliferation of bad bacteria and improve the intraintestinal environment.

The amount of moisture in the intestine also increases (refer to Table 14 and FIG. 6(*b*)), and this improves bowel movements.

Given the above, the intraintestinal environment is improved and intestinal movement is activated, and stress related to the physical condition is nearly eliminated, and this leads to a natural improvement in the absorption of nutrients in the intestine. Therefore, during the first 4 weeks in which stress can increase considerably due to feed changes and the like, it is believed that the piglets of the test section, which did not suffer from much stress, exhibited remarkable increases in body weight compared to the piglets in the control section.

As shown in Table 10, the feed supply rate in the test section was improved compared to the control section during the first 4 weeks. However, during the 4-week period from after 4 weeks to after 8 weeks, and during the 8-week period from the start to after 8 weeks, no improvement was observed in the feed supply rate. This is presumed to be because growth during the first 4 weeks was considerable and the basic metabolism increased due to the piglets actively exercising, and thus the growth body weight gain relative to the feed supply amount was suppressed during the subsequent 4 weeks due to the improvement in the basic metabolism and the increase in the exercise amount. However, since the basic physical strength also improves due to the increase in the exercise amount, etc., it can be anticipated that the feed supply rate will improve and the quality of the meat will be enhanced, etc. after 8 weeks from the start of the test.

According to the formula feed for raising pigs to which 1% by mass of konnyaku fly powder has been added as described above, the period until shipment of the pigs can be shortened, the amount of consumption of the formula feed can be reduced, and the feed-to-sales ratio can be decreased, etc. Further, since the raw ingredient of the konnyaku fly powder is konnyaku, which is the bulb of a plant, the konnyaku fly powder is an extremely safe raw ingredient for the formula feed for raising pigs. In addition, the konnyaku fly powder, which is normally discarded during the manufacture of edible konnyaku, can be effectively utilized.

With regard to a formula feed for raising pigs to which 5% by mass of konnyaku fly powder has been added, although omitted from the test example, this formula feed poses no problems regarding palatability as mentioned above, and the piglets of the test section which were given this formula feed for raising pigs exhibited excellent results in terms of growth body weight gain, amount of feed ingested, feed demand rate, etc. compared to the piglets of the control section which were given the Stock Formula Feeds A and B.

The embodiments and tests described above pertain to an invention related to a formula feed for raising pigs, but effects similar to those achieved by the above formula feed for raising pigs can also be achieved by a formula feed for other animals, a formula feed for livestock, a formula feed for poultry, a formula feed for pets, and a formula feed for culturing fish, etc. which also contain the fly powder. In such cases, for example, for pets such as dogs and cats, by giving a formula feed for pets obtained by mixing, for example, 1 to 5% by mass of fly powder (konnyaku powder is also possible) into a normal formula feed or pet food, etc., the fly powder also functions to absorb bile acid and suppresses to a certain extent the absorption of fats and sugars in the intestine, and thus the intraintestinal environment can be improved. Therefore, such a formula feed for pets can achieve excellent effects of promoting growth while preventing abnormal obesity and promoting health, etc.

A formula feed for raising chickens according to a second embodiment of the present invention will now be explained in detail below referring to the drawings. However, any redundant explanations of elements, etc. which are the same as the constituent elements, etc. indicated above in the first embodiment will be omitted as much as possible.

In the following, a test example using the formula feed for raising chickens comprising a fly powder as well as test results thereof, observations, etc. shall be explained.

(1) Test Facility

Name: Scientific Feeds Research Center of the Japan Scientific Feeds Association Location: 821 Furukura, Narita-shi, Chiba-ken Director: Hisao Itabashi (2) Test Personnel Kenji Komatani, Ken Aoki, Yu Katsunuma, Hirokazu Fujisaki, Kagenari Suga, Koji Hashimoto (3) Test Consignor Shinichiro Ishihashi, Shimonita Bussan Co., Ltd.

(4) Test Execution Period

Jun. 29, 2017 to Aug. 18, 2017 (dates from introduction to sampling of thigh and breast meat)

(5) Test Objective

To examine the effects on growth and health condition, etc. in the case of giving broiler chickens a formula feed for raising chickens containing fly powder.

(6) Materials and Methods (a) Sample Product (Fly Powder)

A konnyaku fly powder provided by Shimonita Bussan Co., Ltd. was used as a sample for testing.

(b) Specimen Baby Chicks 52 newborn male baby chicks of a broiler private species (UK chunky) which had already been vaccinated with live vaccines for Marek's disease and fowlpox at a hatchery were introduced, and after confirming that the baby chicks presented no abnormalities in their health condition, 36 individual chicks weighing between 44 to 50 g were selected for use in the test.

(c) Setting of Testing Sections

The following two sections were set: a control section to which was given a basic feed (Table 15) designed so as to satisfy the required amount of nutrients established in the Japanese Feeding Standard for Poultry (2011 version) (*1); and a test section to which was given a formula feed for raising chickens obtained by adding 1% of the sample product (fly powder) to the basic feed.

The baby chicks were divided into 6 groups of 6 chicks each so as to achieve an even body weight distribution of the specimen baby chicks, and 3 groups were assigned to each of the above-mentioned sections. These sections were raised for 7 weeks from the start of feeding. With regard to the feed, a feed for a fattening first stage was given from the time the baby chicks were divided into groups until 3 weeks after the start of the test, and a feed for a fattening second stage was given from the 4$^{th}$ week after the start of the test (after 3 weeks) until the 7$^{th}$ week after the start of the test (until the end of the test).

TABLE 15

Compounding ratio of basic feed and component composition (%)

| Material | Feed for early fattening stage [1] | Feed for late fattening stage [1] |
|---|---|---|
| Pressed feed corn | 57.96 | 65.83 |
| Grain sorghum | 5.00 | 5.00 |
| Soybean cake | 25.10 | 17.20 |
| Corn gluten meal | 5.00 | 5.00 |
| Fish meal (CP65%) | 1.20 | 2.00 |
| Animal fats and oils | 2.34 | 2.00 |
| Calcium tertiary phosphate | 1.62 | 1.33 |
| Calcium carbonate | 0.76 | 0.66 |
| Salt (high-quality salt) | 0.30 | 0.30 |
| Choline chloride (60% formulation) | 0.05 | — |
| L-Lysine Monohydrochloride | 0.21 | 0.18 |
| DL-Methionine | 0.22 | 0.07 |
| L-Threonine | 0.01 | 0.04 |
| L-Arginine | 0.03 | 0.09 |
| L-Valine | — | 0.10 |
| Vitamin mineral mixture[2] | 0.20 | 0.20 |
| Total | 100.00 | 100.00 |
| Component composition[3] | | |
| Crude protein | 20.52 (103) [4] | 18.19 (114) |
| Metabolic energy (Meal/kg) | 3.112 (100) | 3.174 (102) |
| Calcium | 0.96 (107) | 0.84 (105) |
| Non phytic phosphorus | 0.48 (107) | 0.42 (105) |
| Arginine | 1.21 (100) | 1.07 (100) |
| Glycine + Serine | 1.80 (149) | 1.58 (144) |
| Histidine | 0.51 (150) | 0.45 (155) |
| Isoleucine | 0.79 (101) | 0.68 (100) |
| Leucine | 2.10 (181) | 1.93 (182) |
| Lysine | 1.16 (100) | 0.97 (100) |
| Methionine + Cystine | 0.90 (100) | 0.70 (100) |
| Phenylatanine + Tyrosine | 1.74 (134) | 1.53 (130) |
| Threonine | 0.77 (100) | 0.70 (100) |
| Tryptophan | 0.22 (100) | 0.18 (106) |
| Valine | 0.92 (106) | 0.91 (115) |
| Proline | 1.31 (226) | 1.21 (228) |

Note:
[1] Feed for early fattening stage: From the start of the test until the end of 3 weeks, Feed for late fattening: From 4 weeks to the end of 7 weeks (test end) after the start of the test.
[2] Ingredients contained in 1 kg: Nitric acid thiamine 2 g, Riboflavin 4.5 g, Pyridoxine hydrochloride 2 g, Cyanocobalamin 10 mg, Nicotinic acid 30 g, Calcium D- Pantothenate 7.5 g, d-Biotin 75 mg, Folic acid 1 g, vitamin A 6,500,000 IU, vitamin D3 2,500,000 IU, Acetate dl-α-Tocopherol 40 g, Vitamin K3 3.836 g, Manganese 50 g, Zinc 50 g, Iron 20 g, Copper 7.5 g, Iodine 0.5 g
[3] Calculated value based on Japanese standard feed ingredient table (2009 version)
[4] The FIGURES in parentheses are the percentage of sufficiency with respect to the requested amount of Japanese feeding standard · poultry (2011 version)

"3) values calculated according to the Japanese Feeding Standard Component Table (2009 version) (*2)" in Table 15 above corresponds to the reference document indicated below.

(d) Feeding Management

The specimen baby chicks were raised in their groups for 3 weeks from the start of feeding in an electric heat/hot water supply-type battery system, and then subsequently raised in cages for large chicks until the end of the test. The lights were illuminated all day long, and the baby chicks were able to freely eat feed and drink water. The baby chicks were vaccinated at 4 days old and 15 days old with an NB live vaccine, and at 21 days old with a fowlpox live vaccine.

(7) Survey Items (a) Body Weight and Amount of Body Weight Gain

The body weight of each individual was measured at the time of introduction, at the end of the 3$^{rd}$ week, and at the end of the 7$^{th}$ week, and the group body weight was measured at the end of the 1st week, the 2nd week, the 4th week, the 5th week, and the 6th week. The amount of body weight gain was calculated during the period from the start to the 3rd week (the fattening first stage), the period from the 4th week to the 7th week (the fattening second stage), and for the entire period.

(b) Feed Intake Amount and Feed Demand Rate (Equation 1 Above)

The feed intake amount was measured every week for each group and totaled similar to the amount of body weight gain, and a feed intake amount and feed demand rate per chick was calculated.

(c) Health Condition and Development Rate

The health condition was observed twice each day, in the morning and in the evening. Any dead chickens were autopsied to clarify a cause of death to the extent possible, and the development rate thereof was calculated.

(d) Measurement of Number of Total Bacteria, Number of *Lactobacillus*, and Number of *Bifidobacterium* in Feces/Urine Mixture (*3)

A mixture of feces/urine for measuring the nitrogen-corrected metabolic energy (ME) of the sample feed was collected on the last day of the 7th week. The feces plate was then cleaned and subsequently excreted fresh feces was collected for each group, and the number of bacteria was measured by the following method.

9 mL of an anaerobic diluent was added to a 1 g specimen and then mixed sufficiently to prepare a sample stock solution. Further, the sample stock solution was diluted in a stepwise manner at a common ratio of 10 using the anaerobic diluent under anaerobic conditions to prepare an anaerobic bacterial liquid diluted to $10^{-8}$ times.

The sample stock solution and the diluted anaerobic bacterial liquid were smeared on a BL agar medium (for total number of bacteria and number of *Bifidobacterium*) and an LBS agar medium (for number of *Lactobacillus*), and then anaerobically cultured for 48 hours at 37° C. by a steel wool anaerobic culture method. After culturing, typical colonies which had appeared on the surface of each agar medium were measured, the total number of bacteria, the number of *Lactobacillus*, and the number of *Bifidobacterium* were measured, and the ratio of *Lactobacillus* and *Bifidobacterium* relative to the total number of bacteria was calculated.

(e) Sampling of Breast Meat and Bone-in Thigh Meat

After the body weight measurements at the end of the 7th week, the specimen chickens were made to fast for one night and their body weight during fasting was measured. Subsequently, all of the specimen chickens were slaughtered and drained of blood and samples of the breast meat and the bone-in thigh meat were taken and the weight thereof was measured, and then the weight ratio relative to the fasting body weight was calculated.

The breast meat and the bone-in thigh meat collected from the individual which was the closest to the average body weight in each group were frozen and stored, and then sent by Cool Takkyubin (registered trademark) (i.e. under frozen conditions) to a facility (Wakita Co., Ltd.) instructed by the test consignor.

(f) Measurement of ME of Sample Feed 0.1% of chromium oxide was added to the feed given in the 7th week after the start of the test, and the feces/urine mixture excreted over the three days before the end of feeding was collected from each group. The mixture was forced-air dried for two days at about 60° C., subsequently air dried, and then the portions collected over the three days were mixed and finely pulverized to prepare samples for analysis.

With regard to the sample feed and the feces/urine mixture, the moisture and nitrogen were analyzed according to Feed Analysis Standards (Notice 19 Shoan, No. 14729, by the Director-General of Food Safety and Consumer Affairs Bureau, Ministry of Agriculture, Forestry and Fisheries of Japan dated Apr. 1, 2008), the gross energy (GE) was analyzed with a bomb calorimeter, and the chromium oxide was analyzed by a colorimetric method (*4). The ME of each sample feed was calculated by an index method calculation (*1) using chromium oxide as an indicator, and the metabolic rate (feed ME/feed GE×100) was calculated.

(g) Sending of Feces/Urine Mixture

About 200 g of the urine/feces mixture excreted on the morning of the final day of the 7th week was collected for each group and frozen and stored, and then sent by Cool Takkyubin (registered trademark) (i.e. under frozen conditions) to a facility (Asahi Biowars Co., Ltd.) instructed by the test consignor.

(8) Analysis of Results

The obtained data was examined for significance of the difference between average values with a t-test (*5).

Individuals which died during the test period were excluded from the average values retroactively to the start of the test.

With regard to the effects on growth and health condition, etc. in the case of supplying broiler chickens with a formula feed for raising chickens containing fly powder, the test results and observations, etc. are summarized below.

36 newborn male baby chicks of a broiler private species were used for the test, and a total of two sections were set, i.e. a control section to which was given a basic feed to which the sample product (konnyaku fly powder) was not added, and a test section to which was given the formula feed for raising chickens obtained by adding 1% of the konnyaku fly powder to the basic feed. The specimen baby chicks were divided into 6 groups of 6 chicks each so as to achieve an even body weight distribution of the specimen baby chicks, and 3 repetitive groups were assigned to each of the above-mentioned sections. These sections were raised for 7 weeks from the start of feeding. The growth results were investigated, and then the chickens were slaughtered and drained of blood at the end of the test and their breast meat and bone-in thigh meat were sampled. The urine/feces mixture excreted over the three days before the end the test was collected from each group, and the ME and metabolic rate of each sample feed were calculated by an index method using chromium oxide as an indicator. A fresh feces/urine mixture excreted at the end of the test was also collected for each group, and the total number of bacteria, the number of *Lactobacillus*, and the number of *Bifidobacterium* were measured.

As a result, as shown in Table 16, the amount of body weight gain and the feed intake amount tended to be higher in the test section than in the control section throughout the test period. A significant difference ($p<0.05$) was recognized in the amount of body weight gain during the fattening second stage and over the entire period, and in the feed intake amount over the entire period. No difference was found in the feed demand rate during any of the periods. No abnormalities in the health condition of the specimen chickens were observed in either section.

As shown in Table 17, the total number of bacteria, the number of *Lactobacillus*, and the number of *Bifidobacterium* tended to be higher in the test section compared to the control section. Further, the ratio of *Lactobacillus* and *Bifidobacterium* relative to the total number of bacteria was also higher in the test section than in the control section, and a significant difference (p<0.05) in *Bifidobacterium* was observed.

As shown in Table 18, the weight of the breast meat and the bone-in thigh meat showed a tendency to be heavier in the test section than in the control section. However, no difference was observed in the body weight ratio (weight ratio), which is the ratio of the weight of the bone-in thigh meat relative to the body weight during fasting.

As shown in Table 19, no difference was found in the original ME of the sample feed. However, the dry ME and the metabolic rate were recognized to be superior with a significant difference (p<0.05) in the test section compared to the control section.

The test results and observations thereof will be explained further in the following.

The growth results are as shown in Table 16 (refer to Tables 21 to 24 for more detailed data), and the amount of body weight gain and the feed intake amount tended to be higher in the test section than in the control section throughout the test period. A significant difference (p<0.05) was recognized in the amount of body weight gain during the fattening second stage and over the entire period, and in the feed intake amount over the entire period. No difference was found between the two sections in the feed demand rate during any of the periods.

In other words, even though the feed demand rate was nearly the same, the body weight increase was remarkably higher in the test section to which the konnyaku fly powder was given, and the feed intake amount was also higher in the test section, and these results can be regarded as defining characteristics of the test section.

In the observation of the health condition, one chick (Individual No. 144) in Group 2 of the test section died on the 35$^{th}$ day after the start of the test, and thus this chick was autopsied macroscopically. As a result, no abnormalities were discovered in the major organs, but a large amount of feed remained in the crop, and thus it was presumed that the chick was ingesting the feed until immediately before its death. Therefore, the death was believed to be caused by a sudden death syndrome.

No abnormalities in the health condition were observed in any of the other specimen chickens.

was also higher in the test section than in the control section, and a significant difference (p<0.05) in *Bifidobacterium* was observed. Thus, it can be inferred that proliferation of *Bifidobacterium* was promoted by the sample product (fly powder).

*Lactobacillus* and *Bifidobacterium*, which are good bacteria, were increased in the test section compared to the control section. If good bacteria increase, this also suppresses the increase in bad bacteria, and thus the intraintestinal environment improves, which in turn leads to increases in body weight, etc. The increase in good bacteria is believed to occur because the cellulose included in the konnyaku fly powder changes to oligosaccharides upon entering the intestine through the gastric acid, and the oligosaccharides serve as food for *Bifidobacterium*, etc., which leads to an increase in the amount of good bacteria.

Although subjective, there was a sense that the odor of the feces/urine mixture exhibited a slightly stronger miso-like fermentation odor in the test section, and thus the odor of the feces/urine mixture was less severe compared to the control section.

TABLE 17

Number of bacteria in excreta mixture (1 pgCFU/g)

| Fungus species | Control plot | Test area |
| --- | --- | --- |
| Total bacterial count | 10.04 ± 0.17 | 10.19 ± 0.35 |
| Lactic acid bacteria | 8.76 ± 0.25 (5.8 ± 3.2) | 9.00 ± 0.37 (6.5 ± 1.5) |
| *Bifidobacterium* | 8.37 ± 0.36 (2.2 ± 0.9) | 8.94 ± 0.45 (5.6* ± 1.3) |

Note
1) Average value ± Standard deviation (n = 3)
2) The parenthesis is the ratio (%) to the total number of bacteria calculated from the number of bacteria before the logarithmic transformation
3) *p < 0.05 Significant difference The fasting body weight, the weights of the breast meat and the bone-in thigh meat, and the ratio of the weight of the breast meat or the bone-in thigh meat relative to the fasting body weight (the body weight ratio) are shown in Table 18 (refer to Tables 26 and 27 for more detailed data). The breast meat and the bone-in thigh meat both tended to be heavier in the test section compared to the control section. However, almost no difference was found in the body weight ratio which is the ratio relative to the fasting body weight.

TABLE 16

Developmental results

| Item | Section | Early fattening stage | Late fattening stage | Whole period |
| --- | --- | --- | --- | --- |
| Weight gain | Control plot | 818.4 ± 19.7 | 2462.2 ± 20.4 | 3280.6 ± 29.8 |
| (g/Chick) | Test area | 847.1 ± 48.3 | 2588.1* ± 51.2 | 3435.2* ± 55.1 |
| Feed intake | Control plot | 1077.1 ± 8.7 | 4586.9 ± 25.4 | 5664.0 ± 32.2 |
| (g/Chick) | Test area | 1121.0 ± 63.4 | 4811.7 ± 145.2 | 5932.7 * ± 120.0 |
| Feed conversion ratio | Control plot | 1.32 ± 0.02 | 1.86 ± 0.01 | 1.73 ± 0.01 |
|  | Test area | 1.32 ± 0.02 | 1.86 ± 0.03 | 1.73 ± 0.02 |
| Maturity rate (%) | Control plot | — | — | 100.0 ± 0.0 |
|  | Test area | — | — | 94.4 ± 9.6 |

Note
1) Average value ± Standard deviation (n = 3)
2) *Significant difference (p < 0.05),
3) —: Not calculated The total number of bacteria, the number of *Lactobacillus*, and the number of *Bifidobacterium* in the feces/urine mixture are as shown in Table 17 (refer to Table 25 for more detailed data), and all tended to be greater in the test section than in the control section. Further, the ratio of *Lactobacillus* and *Bifidobacterium* relative to the total number of bacteria The sampling and tasting of the breast meat and bone-in thigh meat were carried out as follows. After the body weight measurements at the end of the$_7$ h week (test), the specimen chickens were made to fast for one night and their body weight during fasting was measured. Subsequently, the specimen chickens were slaughtered and drained of blood and samples of the breast meat and the bone-in thigh meat were taken and the weight thereof was measured, and then the weight ratio relative to the fasting body weight was calculated (Table 18). Testing regarding the taste the breast meat and the bone-in thigh meat was consigned to Wakita (Co., Ltd.), which is a wholesaler of pork and chicken. As a result of the taste tasting, it was reported that the test section was milder in taste and juicier than the control section. In the chickens which were raised by eating the formula feed for raising chickens into which 1% konnyaku fly powder was mixed, the cellulose included in the konnyaku fly powder changes to oligosaccharides upon entering the intestine through the gastric acid, and the oligosaccharides serve as food for the good bacteria *Bifidobacterium* within the intestine. Thus, the amount of good bacteria increases and this improves the intraintestinal environment, and in turn stress levels are reduced and the health condition improves, and this is believed to lead to body weight gains, etc., and also to influence the meat quality resulting in improved meat quality. This improvement in meat quality is thought to improve the taste of the chicken.

TABLE 18

The weight of chicks breast and thigh with bone as well as the ratio of weight to fasting weight

| Section | Fasting weight (g) | Breast meat | | Thigh with bone | |
|---|---|---|---|---|---|
| | | Weight(g) | Weight ratio (%) | Weight(g) | Weight ratio (%) |
| Control plot | 3135.5 ± 51.5 | 529.3 ± 47.8 | 16.9 ± 1.3 | 691.6 ± 13.0 | 22.0 ± 0.7 |
| Test area | 3286.3 ± 57.7 | 558.2 ± 9.8 | 17.2 ± 0.1 | 720.9 ± 21.8 | 21.9 ± 0.5 |

Note)
Average value ± Standard deviation (n = 3)

The GE and ME as well as the metabolic rate of the sample feed are shown in Table 19 (refer to Tables 28 and 29 for more detailed data). No difference between the two sections was observed for the original ME, but the test section was superior with a significant difference (p<0.05) compared to the control section with respect to the dry ME and the metabolic rate.

TABLE 19

GE, ME and metabolic rate of the tested feed

| Section | GE (Mcal/kg) | | ME (Mcal/kg) | | Metabolic rate (%) |
|---|---|---|---|---|---|
| | Original | Dry matter | Original | Dry matter | |
| Control plot | 4.018 | 4.571 | 3.007 ± 0.003 | 3.421* ± 0.004 | 74.84 ± 0.08 |
| Test area | 3.999 | 4.570 | 3.004 ± 0.001 | 3.433 ± 0.001 | 75.11* ± 0.03 |

Note
1) ME and metabolic rate are Average value ± Standard deviation (n = 3),
2) *p < 0.05 Significant difference

TABLE 20

Growth performance

| Item | Section | Starting test~2 weeks | 3 weeks~7 weeks |
|---|---|---|---|
| Weight gain (g/Chick) | Control plot | 381.5 ± 1.5 | 2899.1 ± 30.9 |
| | Test area | 385.8 ± 20.9 | 3049.4* ± 48.2 |
| Feed intake (g/Chick) | Control plot | 473.6 ± 5.5 | 5190.4 ± 37.7 |
| | Test area | 476.3 ± 28.2 | 5456.5* ± 123.4 |

TABLE 20-continued

Growth performance

| Item | Section | Starting test~2 weeks | 3 weeks~7 weeks |
|---|---|---|---|
| Feed conversion ratio | Control plot | 1.24 ± 0.01 | 1.79 ± 0.01 |
| | Test area | 1.23 ± 0.03 | 1.79 ± 0.03 |

Figure 7:
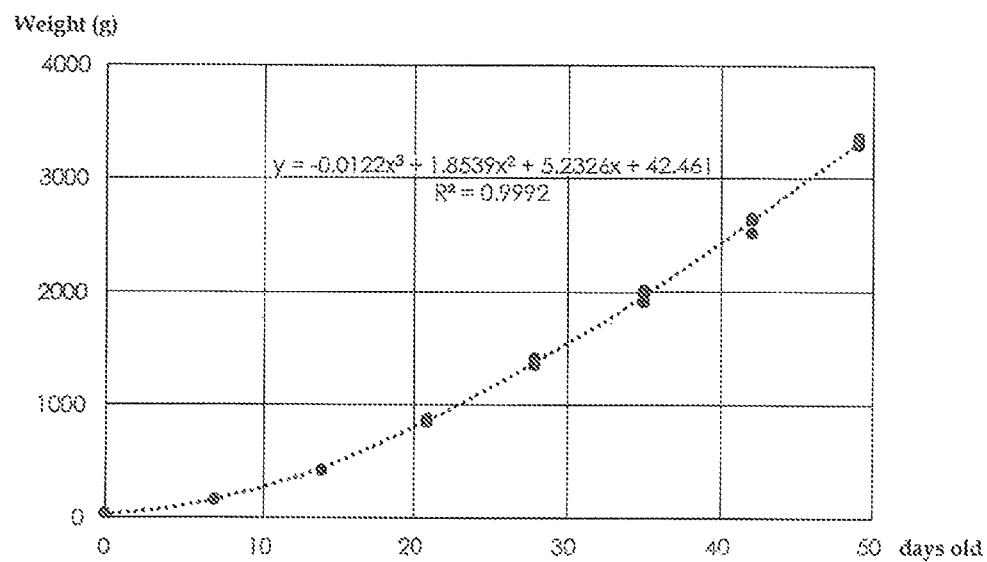
FIG. 7 is a graph illustrating test results showing the relationship between the age in days and the average body weight for baby chicks of a control section which used a conventional formula feed for raising chickens (a basic feed), and further illustrating a cubic regression curve obtained by analysis based on the data of the test results.
Figure 8:
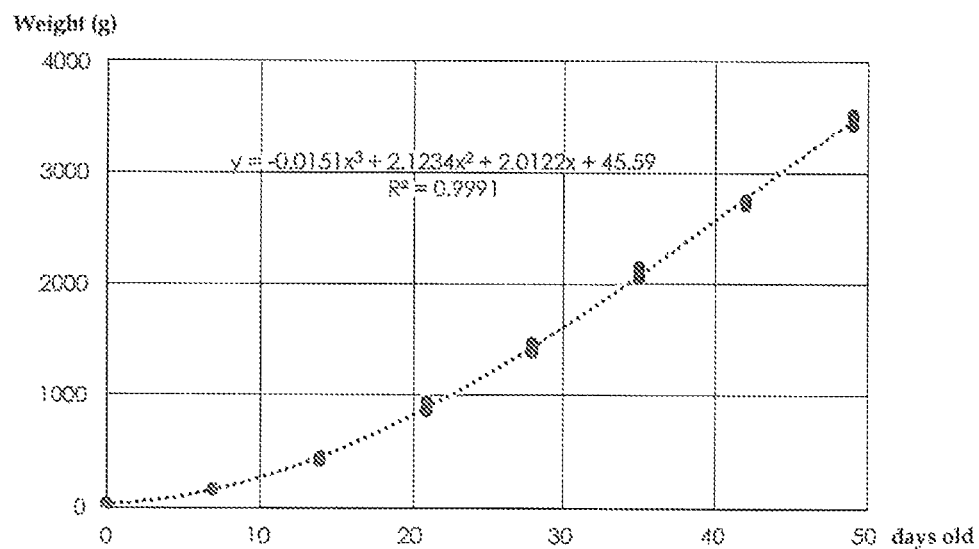
FIG. 8 is a graph illustrating test results showing the relationship between the age in days and the average body weight for baby chicks of a test section which used a formula feed for raising chickens containing fly powder according to a second embodiment of the present invention, and further illustrating a cubic regression curve obtained by analysis based on the data of the test results.

Note
1) Average value ± Standard deviation (n = 3),
2) *p < 0.05 Significant difference With regard to the age in days and the average body weight of each group shown in Table 21, FIGS. 7 and 8 illustrate the test results with regression curves approximated with a cubic expression using a method for curve regression (*5). In Table 21, "start" corresponds to an age in days of "0 days" (an age in weeks of "0 weeks"), an age in weeks of "1 week" corresponds to an age in days of "7 days", an age in weeks of "2 weeks" corresponds to an age in days of "14 days", an age in weeks of "3 weeks" corresponds to an age in days of "21 days", an age in weeks of "4 weeks" corresponds to an age in days of "28 days", an age in weeks of "5 weeks" corresponds to an age in days of "35 days", an age in weeks of "6 weeks" corresponds to an age in days of "42 days", and an age in weeks of "7 weeks" corresponds to an age in days of "49 days". The relationship between these ages in weeks and ages in days is the same in the other tables as well. In Table 21, a development rate of 100% corresponds to a case of normal growth throughout the test period. In Group 2 of the test section, one (Individual No. 144) out of the 6 chicks died on the $35^{th}$ day after the start of the test, and thus the development rate thereof was $(5/6) \times 100 = 83.3\%$.

In FIG. 7, the test results for the age in days and the average body weight of each group (Groups 1 to 3) of the control section shown in Table 21 are respectively allocated to the x-axis and the y-axis. The data of the age in days and the average body weight of each group was plotted, and a cubic regression curve was obtained by the least-squares method on the basis of the above data. Similarly, FIG. 8 illustrates the data of the age in days and the average body weight of each group (Groups 1 to 3) of the test section shown in Table 21 as well as a cubic regression curve thereof. The cubic expressions of the regression curves are as shown in FIGS. 7 and 8.

Since the regression curves are approximated with a cubic expression, two peaks, i.e. a minimum and a maximum, appear, and it is presumed that the minimum peak will occur at the time of 0 days and the maximum peak will occur at the time of the end of growth. Therefore, a cubic expression is one suitable expression for approximating the data over the course of growth. In FIGS. 7 and 8, $R^2$ indicates a determination coefficient (contribution rate) by the square of a correlation coefficient, and as $R^2$ approaches 1, this indicates that the approximate expression more accurately approximates the data. The approximate expression shown in FIG. 7 has an $R^2$ of 0.9992, and the approximate expression shown in FIG. 8 has an $R^2$ of 0.9991. Thus, given these $R^2$ values, it can be said that the regression curves illustrated in FIGS. 7 and 8 accurately approximate the data of the age in days and the average body weight.

Therefore, in the test section to which was given the formula feed for raising chickens containing the fly powder as the sample product, it is believed that the establishment of the indigenous (good) bacteria in the digestive tract was stimulated as compared to the control section, and thus the digestive tract was more suitably maintained which led to an increase in the feed intake amount and an increase in the amount of body weight gain.

Table 22 summarizes the average values for each group of the control section and the test section with regard to the test results of the feed intake amount.

Table 23 summarizes the body weight gain, the feed intake amount, and the feed demand rate during the fattening first stage, the fattening second stage, and the entire period.

With regard to the individual body weight and the body weight gain amount, Table 24 indicates the individual body weight at the start, the $3^{rd}$ week, and the $7^{th}$ week as well as the body weight gain amount during the fattening first stage, the fattening second stage, and the entire period.

Table 25 summarizes the test results for each group regarding the number of bacteria (log CFU/g) in the urine/feces mixture excreted on the morning of the final day of the $7^{th}$ week.

TABLE 21

Average body weight (g) and maturity rate (%)

| Section | Group | Start | 1 week | 2 weeks | 3 weeks | 4 weeks | 5 weeks | 6 weeks | 7 weeks | Maturity rate |
|---|---|---|---|---|---|---|---|---|---|---|
| Control plot | 1 | 46.0 | 163.7 | 428.7 | 880.0 | 1404.5 | 1993.7 | 2636.7 | 3326.7 | 100.0 |
| | 2 | 46.0 | 167.2 | 425.8 | 871.0 | 1415.5 | 2023.2 | 2652.0 | 3356.3 | 100.0 |
| | 3 | 46.3 | 167.3 | 428.3 | 842.5 | 1353.5 | 1918.3 | 2520.5 | 3297.0 | 100.0 |
| | Average | 46.1 | 166.1 | 427.6 | 864.5 | 1391.2 | 1978.4 | 2603.1 | 3326.7 | 100.0 |
| Test area | 1 | 46.0 | 161.2 | 426.0 | 880.7 | 1432.2 | 2093.8 | 2748.0 | 3527.0 | 100.0 |
| | 2 | 46.4 | 162.2 | 414.8 | 852.6 | 1388.2 | 2048.8 | 2692.4 | 3420.4 | 83.3 |
| | 3 | 46.3 | 169.5 | 455.3 | 946.7 | 1475.2 | 2148.7 | 2747.0 | 3496.8 | 100.0 |
| | Average | 46.2 | 164.3 | 432.0 | 893.3 | 1431.9 | 2097.1 | 2729.1 | 3481.4 | 94.1 |

From the regression curves shown in FIGS. 7 and 8, if the shipment body weight is assumed to be 3,000 g, it can be estimated that the control section will reach the shipment body weight at 45.8 days, and the test section will reach the shipment body weight at 44.4 days. Thus, it is recognized that the test section will reach the shipment body weight about 1.4 days faster than the control section.

In chickens, the small intestine microflora of a typical mature chicken is said to be established within 2 weeks after hatching (*6). In this test as well, upon dividing the growth results of the specimen chickens into the period from the start of the test until the $2^{nd}$ week, and from the $3^{rd}$ week until the $7^{th}$ week and comparing the results of these periods, no difference was observed with respect to the feed demand rate as shown in Table 20. However, with regard to the body weight gain and the feed intake amount, although no large difference was seen between the two sections in the period from the start of the test until the $2^{nd}$ week, a sufficiently large difference with 5% significance was recognized in the test section as compared to the control section during the period from the $3^{rd}$ week to the $7^{th}$ week.

Table 26 shows the test results regarding the weight of the left and right breast meat and the total weight thereof, the fasting body weight, and the ratio (weight ratio) of the total weight of the breast meat relative to the fasting body weight.

Table 27 shows the test results regarding the weight of the left and right bone-in thigh meat and the total weight thereof, the fasting body weight, and the ratio (weight ratio) of the total weight of the bone-in thigh meat relative to the fasting body weight.

Table 28 summarizes the analysis values including the gross energy GE as well as the analysis values for the feces/urine mixture for the basic feed given to the control section and the formula feed for raising chickens (obtained by adding 1% fly powder to the basic feed) given to the test section.

Table 29 summarizes the analysis values in each group for the metabolic energy ME of the basic feed given to the control section and the formula feed for raising chickens given to the test section, as well as the metabolic rate of each group. The metabolic rate was calculated as (ME/GE)× 100% on the basis of the dry product.

TABLE 22

Feed intake (g/chick)

| Section | Group | 1 week | 2 weeks | 3 weeks | 4 weeks | 5 weeks | 6 weeks | 7 weeks |
|---|---|---|---|---|---|---|---|---|
| Control plot | 1 | 136.1 | 338.2 | 607.8 | 926.8 | 1079.0 | 1205.8 | 1368.0 |
| | 2 | 123.6 | 344.2 | 614.3 | 920.0 | 1087.5 | 1224.7 | 1383.0 |
| | 3 | 133.0 | 345.7 | 588.3 | 880.2 | 1061.7 | 1173.8 | 1450.3 |
| | Average | 130.9 | 342.7 | 603.5 | 909.0 | 1076.1 | 1201.4 | 1400.4 |
| Test area | 1 | 129.7 | 350.2 | 636.7 | 955.8 | 1149.8 | 1303.8 | 1544.3 |
| | 2 | 116.6 | 329.8 | 613.5 | 920.8 | 1133.7 | 1268.2 | 1495.4 |
| | 3 | 132.7 | 369.8 | 684.0 | 949.5 | 1161.0 | 1151.2 | 1401.7 |
| | Average | 126.3 | 349.9 | 644.7 | 942.0 | 1148.2 | 1241.1 | 1480.5 |

TABLE 23

Weight gain, feed intake and feed conversion ratio

| | | Weight gain (g/Chick) | | | Feed intake (g/Chick) | | | Feed conversion ratio | | |
|---|---|---|---|---|---|---|---|---|---|---|
| Section | Group | The first term | The latter term | Whole period | The first term | The latter term | Whole period | The first term | The latter term | Whole period |
| Control plot | 1 | 834.0 | 2446.7 | 3280.7 | 1082.1 | 4579.6 | 5661.7 | 1.30 | 1.87 | 1.73 |
| | 2 | 825.0 | 2485.3 | 3310.3 | 1082.1 | 4615.2 | 5697.3 | 1.31 | 1.86 | 1.72 |
| | 3 | 796.2 | 2454.5 | 3250.7 | 1067.0 | 4566.0 | 5633.0 | 1.34 | 1.86 | 1.73 |
| | Average | 818.4 | 2462.2 | 3280.6 | 1077.1 | 4586.9 | 5664.0 | 1.32 | 1.86 | 1.73 |
| Test area | 1 | 834.7 | 2646.3 | 3481.0 | 1116.6 | 4953.7 | 6070.3 | 1.34 | 1.87 | 1.74 |
| | 2 | 806.2 | 2567.8 | 3374.0 | 1059.9 | 4818.1 | 5878.0 | 1.31 | 1.88 | 1.74 |
| | 3 | 900.3 | 2550.2 | 3450.5 | 1186.5 | 4663.4 | 5849.9 | 1.32 | 1.83 | 1.70 |
| | Average | 847.1 | 2588.1 | 3435.2 | 1121.0 | 4811.7 | 5932.7 | 1.32 | 1.86 | 1.73 |

TABLE 24

Individual weight and weight gain (g)

| | | | Weight | | | Weight gain | | |
|---|---|---|---|---|---|---|---|---|
| Section | Group | Individual number | Start | 3 weeks | 7 weeks | The first term | The letter term | Whole period |
| Control plot | 1 | 118 | 44 | 732 | 2878 | 688 | 2146 | 2834 |
| | | 119 | 44 | 732 | 3091 | 688 | 2359 | 3047 |
| | | 120 | 44 | 842 | 3019 | 798 | 2177 | 2975 |
| | | 121 | 46 | 989 | 3930 | 943 | 2941 | 3884 |
| | | 122 | 48 | 1011 | 3671 | 963 | 2660 | 3623 |
| | | 123 | 50 | 974 | 3371 | 924 | 2397 | 3321 |
| | | Average | 46.0 | 880.0 | 3326.7 | 834.0 | 2446.7 | 3280.7 |
| | 2 | 124 | 44 | 1020 | 3730 | 976 | 2710 | 3686 |
| | | 125 | 44 | 854 | 3645 | 810 | 2791 | 3601 |
| | | 126 | 44 | 846 | 2901 | 802 | 2055 | 2857 |
| | | 127 | 46 | 1023 | 3572 | 977 | 2549 | 3526 |
| | | 128 | 48 | 942 | 3755 | 894 | 2813 | 3707 |
| | | 129 | 50 | 541 | 2535 | 491 | 1994 | 2485 |
| | | Average | 46.0 | 871.0 | 3356.3 | 825.0 | 2485.3 | 3310.3 |
| | 3 | 130 | 44 | 731 | 3132 | 687 | 2401 | 3088 |
| | | 131 | 44 | 824 | 3007 | 780 | 2183 | 2963 |
| | | 132 | 46 | 989 | 3513 | 943 | 2524 | 3467 |
| | | 133 | 46 | 902 | 3359 | 856 | 2457 | 3313 |
| | | 134 | 48 | 994 | 3913 | 946 | 2919 | 3865 |
| | | 135 | 50 | 615 | 2858 | 565 | 2243 | 2808 |
| | | Average | 46.3 | 842.5 | 3297.0 | 796.2 | 2454.5 | 3250.7 |
| | Average | | 46.1 | 864.5 | 3326.7 | 818.4 | 2462.2 | 3280.6 |
| Test area | 1 | 136 | 44 | 885 | 3875 | 841 | 2990 | 3831 |
| | | 137 | 44 | 871 | 3307 | 827 | 2436 | 3263 |
| | | 138 | 44 | 938 | 3876 | 894 | 2938 | 3832 |
| | | 139 | 46 | 912 | 3424 | 866 | 2512 | 3378 |
| | | 140 | 48 | 685 | 3041 | 637 | 2356 | 2993 |
| | | 141 | 50 | 993 | 3639 | 943 | 2646 | 3589 |
| | | Average | 46.0 | 880.7 | 3527.0 | 834.7 | 2646.3 | 3481.0 |

TABLE 24-continued

Individual weight and weight gain (g)

| Section | Group | Individual number | Weight Start | Weight 3 weeks | Weight 7 weeks | Weight gain The first term | Weight gain The letter term | Weight gain Whole period |
|---|---|---|---|---|---|---|---|---|
| | 2 | 142 | 44 | 826 | 3737 | 782 | 2911 | 3693 |
| | | 143 | 44 | 729 | 3012 | 685 | 2283 | 2968 |
| | | 144 | 44 | 868 | Death | 824 | Death | Death |
| | | 145 | 46 | 776 | 3480 | 730 | 2704 | 3434 |
| | | 146 | 48 | 842 | 3113 | 794 | 2271 | 3065 |
| | | 147 | 50 | 1090 | 3760 | 1040 | 2670 | 3710 |
| | | Average | 46.4 | 852.6 | 3420.4 | 806.2 | 2567.8 | 3374.0 |
| | 3 | 148 | 44 | 1143 | 4215 | 1099 | 3072 | 4171 |
| | | 149 | 44 | 930 | 3040 | 886 | 2110 | 2996 |
| | | 150 | 46 | 936 | 3741 | 890 | 2805 | 3695 |
| | | 151 | 46 | 834 | 3291 | 788 | 2457 | 3245 |
| | | 152 | 48 | 950 | 3538 | 902 | 2588 | 3490 |
| | | 153 | 50 | 887 | 3156 | 837 | 2269 | 3106 |
| | | Average | 46.3 | 946.7 | 3496.8 | 900.3 | 2550.2 | 3450.5 |
| | | Average | 46.2 | 893.3 | 3481.4 | 847.1 | 2588.1 | 3435.2 |

Note)
Since the individual number 144 of the 2th group of the test area was dead on the 35th day after the start of the test, it was excluded from the average value retroactively.

TABLE 25

Number of bacteria in excreta mixture (1 pgCFU/g)

| Section | Group | Total bacterial count | Lactic acid bacteria | Bifidobacterium |
|---|---|---|---|---|
| Control plot | 1 | 9.91 | 8.88 (9.4) | 8.00 (1.2) |
| | 2 | 10.24 | 8.93 (4.8) | 8.71 (2.9) |
| | 3 | 9.98 | 8.48 (3.2) | 8.40 (2.6) |
| | Average | 10.04 | 8.76 (5.8) | 8.37 (2.2) |
| Test area | 1 | 9.98 | 8.88 (7.9) | 8.66 (4.8) |
| | 2 | 10.60 | 9.42 (6.6) | 9.45 (7.1) |
| | 3 | 10.00 | 8.70 (5.0) | 8.70 (5.0) |
| | Average | 10.19 | 9.00 (6.5) | 8.94 (5.6) |

Note)
The parenthesis is the ratio (%) to the total number of bacteria calculated from the number of bacteria before the logarithmic transformation

TABLE 26

The weight of chicks breast and the ratio of weight to fasting weight

| Section | Group | Individual number | Fasting weight (g) | Weight (g) Right | Weight (g) Left | Weight (g) Total | Weight ratio (%) |
|---|---|---|---|---|---|---|---|
| Control plot | 1 | 118 | 2684 | 229 | 221 | 450 | 16.8 |
| | | 119 | 2905 | 254 | 246 | 500 | 17.2 |
| | | 120 | 2824 | 208 | 204 | 412 | 14.6 |
| | | 121 | 3759 | 304 | 292 | 596 | 15.9 |
| | | 122 | 3486 | 316 | 326 | 642 | 18.4 |
| | | 123 | 3198 | 256 | 218 | 474 | 14.8 |
| | | Average | 3142.7 | 261.2 | 251.2 | 512.3 | 16.3 |
| | 2 | 124 | 3554 | 334 | 364 | 698 | 19.6 |
| | | 125 | 3447 | 338 | 357 | 695 | 20.2 |
| | | 126 | 2744 | 246 | 237 | 483 | 17.6 |
| | | 127 | 3371 | 381 | 291 | 672 | 19.9 |
| | | 128 | 3542 | 321 | 326 | 647 | 18.3 |
| | | 129 | 2440 | 156 | 149 | 305 | 12.5 |
| | | Average | 3183.0 | 296.0 | 287.3 | 583.3 | 18.3 |
| | 3 | 130 | 2969 | 200 | 193 | 393 | 13.2 |
| | | 131 | 2812 | 243 | 214 | 457 | 16.3 |
| | | 132 | 3275 | 277 | 272 | 549 | 16.8 |
| | | 133 | 3169 | 289 | 279 | 568 | 17.9 |
| | | 134 | 3612 | 328 | 300 | 628 | 17.4 |
| | | 135 | 2648 | 177 | 182 | 359 | 13.6 |
| | | Average | 3080.8 | 252.3 | 240.0 | 492.3 | 16.0 |
| | Average | | 3135.5 | 269.8 | 259.5 | 529.3 | 16.9 |
| Test area | 1 | 136 | 3696 | 329 | 304 | 633 | 17.1 |
| | | 137 | 3090 | 256 | 235 | 491 | 15.9 |
| | | 138 | 3669 | 318 | 303 | 621 | 16.9 |
| | | 139 | 3254 | 317 | 318 | 635 | 19.5 |
| | | 140 | 2808 | 222 | 206 | 428 | 15.2 |
| | | 141 | 3455 | 310 | 299 | 609 | 17.6 |
| | | Average | 3328.7 | 292.0 | 277.5 | 569.5 | 17.1 |
| | 2 | 142 | 3525 | 311 | 315 | 626 | 17.8 |
| | | 143 | 2768 | 222 | 234 | 456 | 16.5 |
| | | 144 | Death | — | — | — | — |
| | | 145 | 3250 | 291 | 281 | 572 | 17.6 |
| | | 146 | 2942 | 235 | 222 | 457 | 15.5 |
| | | 147 | 3618 | 326 | 326 | 652 | 18.0 |
| | | Average | 3220.6 | 277.0 | 275.6 | 552.6 | 17.2 |
| | 3 | 148 | 3945 | 370 | 353 | 723 | 18.3 |
| | | 149 | 2962 | 202 | 196 | 398 | 13.4 |
| | | 150 | 3502 | 295 | 355 | 650 | 18.6 |
| | | 151 | 3126 | 299 | 289 | 588 | 18.8 |
| | | 152 | 3340 | 292 | 265 | 557 | 16.7 |
| | | 153 | 2983 | 257 | 255 | 512 | 17.2 |
| | | Average | 3309.7 | 285.8 | 285.5 | 571.3 | 17.3 |
| | Average | | 3286.3 | 284.9 | 279.5 | 558.2 | 17.2 |

TABLE 27

The weight of thigh with bone and the ratio of the weight to the body weight at the time of fasting

| Section | Group | Individual number | Fasting weight (g) | Weight (g) Right | Weight (g) Left | Weight (g) Total | Weight ratio (%) |
|---|---|---|---|---|---|---|---|
| Control plot | 1 | 118 | 2684 | 285 | 268 | 553 | 20.6 |
| | | 119 | 2905 | 314 | 318 | 632 | 21.8 |
| | | 120 | 2824 | 301 | 332 | 633 | 22.4 |
| | | 121 | 3759 | 414 | 383 | 797 | 21.2 |

TABLE 27-continued

The weight of thigh with bone and the ratio of the weight to the body weight at the time of fasting

| Section | Group | Individual number | Fasting weight (g) | Weight (g) Right | Left | Total | Weight ratio (%) |
|---|---|---|---|---|---|---|---|
| | | 122 | 3486 | 368 | 377 | 745 | 21.4 |
| | | 123 | 3198 | 352 | 351 | 703 | 22.0 |
| | | Average | 3142.7 | 339.0 | 338.2 | 677.2 | 21.5 |
| | 2 | 124 | 3554 | 350 | 349 | 699 | 19.7 |
| | | 125 | 3447 | 360 | 370 | 730 | 21.2 |
| | | 126 | 2744 | 306 | 306 | 612 | 22.3 |
| | | 127 | 3371 | 384 | 394 | 778 | 23.1 |
| | | 128 | 3542 | 396 | 398 | 794 | 22.4 |
| | | 129 | 2440 | 278 | 281 | 559 | 22.9 |
| | | Average | 3183.0 | 345.7 | 349.7 | 695.3 | 21.8 |
| | 3 | 130 | 2969 | 351 | 345 | 696 | 23.4 |
| | | 131 | 2812 | 301 | 307 | 608 | 21.6 |
| | | 132 | 3275 | 360 | 382 | 742 | 22.7 |
| | | 133 | 3169 | 374 | 367 | 741 | 23.4 |
| | | 134 | 3612 | 400 | 390 | 790 | 21.9 |
| | | 135 | 2648 | 324 | 313 | 637 | 24.1 |
| | | Average | 3080.8 | 351.7 | 350.7 | 702.3 | 22.8 |
| | Average | | 3135.5 | 345.5 | 346.2 | 691.6 | 22.0 |
| Test area | 1 | 136 | 3696 | 399 | 409 | 808 | 21.9 |
| | | 137 | 3090 | 371 | 380 | 751 | 24.3 |
| | | 138 | 3669 | 412 | 402 | 814 | 22.2 |
| | | 139 | 3254 | 336 | 330 | 666 | 20.5 |
| | | 140 | 2808 | 312 | 306 | 618 | 22.0 |
| | | 141 | 3455 | 406 | 413 | 819 | 23.7 |
| | | Average | 3328.7 | 372.7 | 373.3 | 746.0 | 22.4 |
| | 2 | 142 | 3525 | 373 | 382 | 755 | 21.4 |
| | | 143 | 2768 | 304 | 307 | 611 | 22.1 |
| | | 144 | Death | — | — | — | — |
| | | 145 | 3250 | 341 | 339 | 680 | 20.9 |
| | | 146 | 2942 | 340 | 329 | 669 | 22.7 |
| | | 147 | 3618 | 412 | 406 | 818 | 22.6 |
| | | Average | 3220.6 | 354.0 | 352.6 | 706.6 | 21.9 |
| | 3 | 148 | 3945 | 428 | 429 | 857 | 428 |
| | | 149 | 2962 | 261 | 268 | 529 | 261 |
| | | 150 | 3502 | 383 | 399 | 782 | 383 |
| | | 151 | 3126 | 337 | 323 | 660 | 337 |
| | | 152 | 3340 | 377 | 382 | 759 | 377 |
| | | 153 | 2983 | 333 | 340 | 673 | 333 |
| | | Average | 3309.7 | 353.2 | 356.8 | 710.0 | 21.5 |
| | Average | | 3286.3 | 360.0 | 360.9 | 720.9 | 21.9 |

TABLE 28

Analytical values of test feed and excreta mixture

| Section | Sample | Nitrogen(%) | Total energy (Mcal/kg) | Chromium oxide (%) |
|---|---|---|---|---|
| Control plot | Feed | 3.01 | 4.018 | 0.100 |
| | Excreta mixture 1 group | 5.22 | 3.96 | 0.464 |
| | 2 group | 5.01 | 3.94 | 0.460 |
| | 3 group | 5.51 | 3.93 | 0.456 |
| Test area | Feed | 2.89 | 3.999 | 0.108 |
| | Excreta mixture 1 group | 4.94 | 3.90 | 0.499 |
| | 2 group | 4.81 | 3.92 | 0.502 |
| | 3 group | 5.18 | 3.90 | 0.495 |

TABLE 29

Metabolic energy and metabolic rate of the tested feed

| Section | Group | Metabolic energy (Mcal/kg) Original | Dry matter | Metabolic rate (%) |
|---|---|---|---|---|
| Control plot | 1 | 3.010 | 3.424 | 74.9 |
| | 2 | 3.004 | 3.417 | 74.8 |
| | 3 | 3.010 | 3.422 | 74.9 |
| | Average | 3.009 | 3.421 | 74.9 |
| Test area | 1 | 3.006 | 3.434 | 75.2 |
| | 2 | 3.004 | 3.432 | 75.1 |
| | 3 | 3.004 | 3.432 | 75.1 |
| | Average | 3.005 | 3.433 | 75.1 |

(*1) to (*6) indicated above correspond to the following reference documents.

(*1) Japanese Feeding Standard Component Table (2009 version) edited by the National Agriculture and Food Research Organization (Incorporated Administrative Agency), Japan Livestock Industry Association, Tokyo, 2010.

(*2) Japanese Feeding Standard for Poultry (2011 version) edited by the National Agriculture and Food Research Organization (Incorporated Administrative Agency), Japan Livestock Industry Association, Tokyo, 2012.

(*3) Tomotari Mitsuoka, et al., Classification and Identification of Anaerobic Bacteria (edited by the Education Board of the Japan Society of Bacteriology), Saikon Publishing Co., Tokyo, 1982.

(*4) Masaaki Takemasa: Improvement of the Method for Chromic Oxide Determination with Potassium Phosphate Reagent, Bulletin of National Institute of Animal Industry 52, 1992.

(*5) Minoru Yoshioka: Design of Experiments for Animal Husbandry, Yokendo, Tokyo, 1998.

(*6) Japan Chunky Association: Gut Health in Poultry—The World Within, Ross Tech Note—Gut Health in Poultry, August 2013, 2013.

The invention claimed is:

1. A formula feed characterized in that among a refined powder and a fly powder which are obtained by pulverizing konnyaku (*arum* root), which is a bulb of a plant, wherein the fly powder is added to the formula feed.

2. The formula feed according to claim 1, wherein at least 1% by mass of the fly powder is added.

3. A formula feed for raising pigs characterized in that the formula feed according to claim 2.

4. A formula feed for raising chickens characterized in that the formula feed according to claim 2.

5. The formula feed according to claim 1, wherein 1 to 5% by mass of the fly powder is added.

6. A formula feed for raising pigs characterized in that the formula feed according to claim 5.

7. A formula feed for raising chickens characterized in that the formula feed according to claim 5.

8. The formula feed according to claim 1, wherein the fly powder corresponds to 40 to 50% of the total mass of the fly powder and the refined powder.

9. The formula feed according to claim 8, wherein at least 1% by mass of the fly powder is added.

10. A formula feed for raising pigs characterized in that the formula feed according to claim 9.

11. A formula feed for raising chickens characterized in that the formula feed according to claim 9.

12. The formula feed according to claim 8, wherein 1 to 5% by mass of the fly powder is added.

13. A formula feed for raising pigs characterized in that the formula feed according to claim 12.

14. A formula feed for raising chickens characterized in that the formula feed according to claim 12.

15. A formula feed for raising pigs characterized in that the formula feed according to claim 8.

16. A formula feed for raising chickens characterized in that the formula feed according to claim 8.

17. A formula feed for raising pigs characterized in that the formula feed according to claim 1.

18. A formula feed for raising chickens characterized in that the formula feed according to claim 1.

* * * * *